United States Patent

Kondoh

Patent Number: 5,853,930
Date of Patent: Dec. 29, 1998

[54] ELECTROPHOTOGRAPHIC PHOTOCONDUCTORS USING BISAZO COMPOUNDS

[75] Inventor: Akihiro Kondoh, Nara, Japan

[73] Assignee: Sharp Kabushiki Kaisha, Osaka, Japan

[21] Appl. No.: 768,233

[22] Filed: Dec. 17, 1996

[30] Foreign Application Priority Data

Dec. 22, 1995 [JP] Japan ................................. 7-335307

[51] Int. Cl.⁶ .................................................. G03G 5/06
[52] U.S. Cl. ................................. 430/58; 430/73; 430/75
[58] Field of Search ................................. 430/73, 75, 58

[56] References Cited

U.S. PATENT DOCUMENTS

| | | | |
|---|---|---|---|
| 5,194,353 | 3/1993 | Tawaka et al. | 430/75 |
| 5,219,688 | 6/1993 | Kashizaki et al. | 430/75 |

FOREIGN PATENT DOCUMENTS 0034498B  8/1981  European Pat. Off. .

OTHER PUBLICATIONS

*Patent Abstracts of Japan*, vol. 17, No. 588 (P–1634), 27 Oct. 1993 (JP 05–173344 A).

Otto Dan et al., "Synthesen biskationischer, trypanocider 1–Benzofuran–Verbindungen", *Liebigs Annalen Der Chemie*, vol. 10, 1982, Weinheim DE, pp. 1836–1869.

J. D. Loudon et al., "Dibenz(b,f)oxepins and Related Compounds", *Journal of the Chemical Society*, 1957, Letchworth, GB, pp. 3809–3813.

*Primary Examiner*—John Goodrow
*Attorney, Agent, or Firm*—Birch, Stewart, Kolasch & Birch, LLP

[57] ABSTRACT

There is provided an electrophotographic photoconductor comprising as a charge carrier generating substance a bisazo compound of the general formula (I):

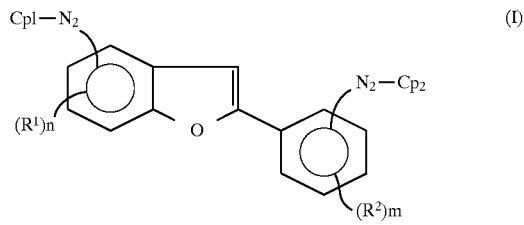

wherein $R^1$ and $R^2$ are the same or different, each representing a hydrogen atom, a halogen atom, a lower alkyl group optionally substituted with a fluorine atom, an aralkyl group optionally having a substituent, a lower alkoxy group, or a di-(lower alkyl)amino group; n is an integer from 1 to 3; m is an integer from 1 to 4; and Cp1 and Cp2 are the same or different, each representing an aromatic condensed heterocyclic or aromatic condensed hydrocarbon residue having at least one phenolic hydroxyl group and optionally having a substituted carbamoyl group or a heterocyclic group.

9 Claims, 8 Drawing Sheets

ELECTROPHOTOGRAPHIC PHOTOCONDUCTORS USING BISAZO COMPOUNDS

BACKGROUND OF THE INVENTION

1. Field of the Invention

The present invention relates to an electrophotographic photoconductor using a bisazo compound. More particularly, the invention relates to an electrophotographic photoconductor using a bisazo compound as a charge carrier generating substance or charge carrier transferring substance and further the bisazo compound as well as a process for producing the same.

2. Related Art

A variety of electrophotographic processes are now available, among which a direct system, a latent image transferring system and the like are well known. Fundamental properties required for an electrophotoconductive substance constituting an electrophotoconductive layer of an electrophotographic photoconductor for use in these electrophotographic processes are as follows:

(1) A high electrostatic chargeability of an electric charge generated by corona discharge in a dark place;

(2) A smaller reduction in the electric charge thus generated by corona discharge in the dark place;

(3) A quick dissipation of the electric charge by illumination;

(4) A reduced residual charge after the illumination;

(5) A smaller increase in the residual potential and a smaller reduction in the initial potential through repetitive use thereof; and (6) A smaller change in the electrophotographic characteristics due to an influence of ambient temperature and humidity.

Inorganic materials such as zinc oxide (Japanese Examined Patent Publication No. 57-19780 (1982)), cadmium sulfide (Japanese Examined Patent Publication No. 58-46018 (1983)) and amorphous selenium alloys have been employed as electrophotoconductive substances which satisfy the aforesaid requirements. However, various drawbacks of these electrophotoconductive substances have recently been pointed out. The zinc oxide based material requires addition of a sensitizer for enhancement of the photosensitivity thereof. Since the sensitizer reduces electrostatic chargeability of an electric charge generated by corona discharge and causes discoloration by light exposure, the zinc oxide based material fails to provide stable images over a prolonged period. The cadmium sulfide based material fails to offer a stable photosensitivity under a humid condition. The selenium based material has a high toxicity and a poor thermal stability, and the crystallization thereof readily promoted by such external factors as temperature and humidity reduces the electrostatic chargeability, resulting in formation of white spots in an image. Further, the production of the selenium based material requires difficult production conditions.

In view of the future prospect, organic electrophotoconductive substances are more desirable for use in electrophotographic photoconductors than inorganic ones which are limited in production with concern for the depletion of natural resources and are more likely to cause pollution due to the toxicity thereof to raise an environmental concern. Therefore, researches have been made on electrophotographic photoconductors employing various organic compounds. In recent years, the research and development have positively introduced concepts of function-separated photoconductors. One dominant concept is a photoconductor of the type which has a charge carrier generating layer and a charge carrier transferring layer of hole migration type stacked on a conductive support base in this order and is adapted to negatively charge the surface of the charge carrier transferring layer.

This concept has allowed for independent development of substances having a charge carrier generating function and substances having a charge carrier transferring function. As a result, charge carrier generating substances and charge carrier transferring substances of various molecular structures have been developed.

Examples of charge carrier generating substances so far developed (particularly bisazo compounds which are herein classified on the basis of structural characteristics of azo bases thereof) include benzidine compounds (Japanese Unexamined Patent Publication No. 47-37543 (1972)), stilbene compounds (Japanese Unexamined Patent Publication No. 60-27014 (1985)), oxadiazole compounds (Japanese Unexamined Patent Publication No. 60-27016 (1985)), fluorene compounds (Japanese Unexamined Patent Publication No. 60-28344 (1985)), fluorenone compounds (Japanese Unexamined Patent Publication No. 60-29109 (1985)), dibenzothiophene compounds (Japanese Unexamined Patent Publication No. 60-27108 (1985)), dibenzothiophenesulfone compounds (Japanese Unexamined Patent Publication No. 60-29108 (1985)), naphthoxazole compounds (Japanese Unexamined Patent Publication No. 61-34675 (1986)), bisstilbene compounds (Japanese Unexamined Patent Publication No. 61-29499 (1986)), N-alkylcarbazole compounds (Japanese Unexamined Patent Publication No. 62-19744 (1987)), and anthraquinone compounds (Japanese Unexamined Patent Publication No. 62-30264 (1987)).

Although many organic compounds have been developed as charge carrier generating substances, none of the bisazo compounds so far developed solve all the following problems:

(1) A change in the photosensitivity through repetitive use;

(2) A low electrostatic chargeability and poor repetitive charging characteristics; and (3) Poor residual potential characteristics.

An organic compound has not been developed yet which satisfies the aforesaid fundamental property requirements for a photoconductor and offers a high mechanical strength and durability. It is therefore desired to develop an excellent organic electrophotoconductive substance and photoconductor.

Further, azo bases for a charge carrier generating substance and a charge carrier transferring substance are produced from different materials through different production processes and, therefore, require an increased production cost.

SUMMARY OF THE INVENTION

As a result of intensive studies on electrophotoconductive substances having a high photosensitivity and an excellent durability, the inventors of the present invention have found that a novel bisazo compound of the formula (I) is very useful as an electrophotoconductive substance, and achieved the present invention.

In accordance with a first aspect of the present invention, there is provided an electrophotographic photoconductor comprising as a charge carrier generating substance a bisazo compound of the general formula (I):

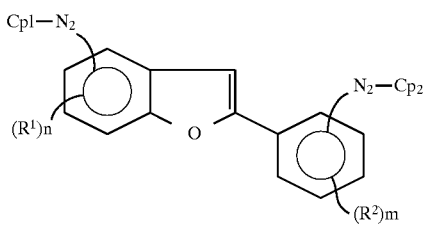   (I)

wherein $R^1$ and $R^2$ are the same or different, each representing a hydrogen atom, a halogen atom, a lower alkyl group optionally substituted with a fluorine atom, an aralkyl group optionally having a substituent, a lower alkoxy group, or a di-(lower alkyl)amino group; n is an integer from 1 to 3; m is an integer from 1 to 4; and Cp1 and Cp2 are the same or different, each representing an aromatic condensed heterocyclic or aromatic condensed hydrocarbon residue having at least one phenolic hydroxyl group and optionally having a substituted carbamoyl group or a heterocyclic group.

In accordance with a second aspect of the present invention, there is provided a bisazo compound of the general formula (I):

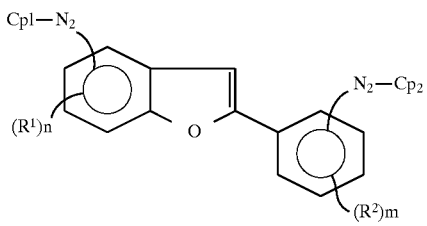   (I)

wherein $R^1$ and $R^2$ are the same or different, each representing a hydrogen atom, a halogen atom, a lower alkyl group optionally substituted with a fluorine atom, an aralkyl group optionally having a substituent, a lower alkoxy group, or a di-(lower alkyl)amino group; n is an integer from 1 to 3; m is an integer from 1 to 4; and Cp1 and Cp2 are the same or different, each representing an aromatic condensed heterocyclic or aromatic condensed hydrocarbon residue having at least one phenolic hydroxyl group and optionally having a substituted carbamoyl group or a heterocyclic group.

In accordance with a third aspect of the present invention, there is provided a process for producing the bisazo compound (I) comprising the steps of:

reacting a nitrosalicylaldehyde derivative of the general formula (II):

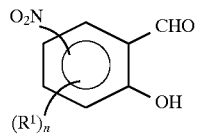   (II)

wherein $R^1$ is representing a hydrogen atom, a halogen atom, a lower alkyl group optionally substituted with a fluorine atom, an aralkyl group optionally having a substituent, a lower alkoxy group, or a di-(lower alkyl) amino group; n is an integer from 1 to 3, with a nitrobenzyl halide derivative of the general formula (III):

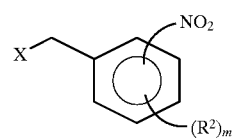   (III)

wherein X is a halogen atom, and $R^2$ is a hydrogen atom, a halogen atom, a lower alkyl group optionally substituted with a fluorine atom, an aralkyl group optionally having a substituent, a lower alkoxy group, or a di-(lower alkyl) amino group; n is an integer from 1 to 3 and m is an integer from 1 to 4 to provide a 2-(nitrobenzyloxy) nitrobenzaldehyde derivative of the general formula (IV):

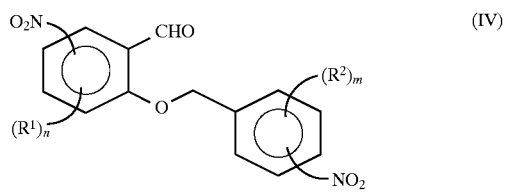   (IV)

wherein $R^1$, $R^2$, n and m each have the same definition as described above;

reacting the 2-(nitrobenzyloxy) nitrobenzaldehyde derivative in the presence of a condensing agent for intramolecular cyclization to provide a 2-(nitrophenyl) nitrobenzo[b]furan derivative of the general formula (V):

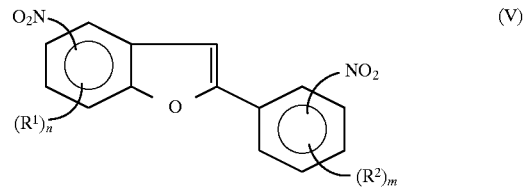   (V)

wherein $R^1$, $R^2$, n and m each have the same definition as described above;

reducing the 2-(nitrophenyl)nitrobenzo[b]furan derivative to provide a 2-(aminophenyl)aminobenzo[b]furan derivative of the general formula (VI):

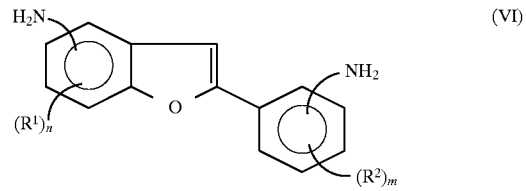   (VI)

wherein $R^1$, $R^2$, n and m each have the same definition as described above;

tetra-azotizing the 2-(aminophenyl)aminobenzo [b]furan derivative; and coupling the tetra-azotized 2-(aminophenyl) aminobenzo [b]furan derivative with a coupling agent Cp1-Y or Cp2-Y wherein Y is a hydrogen atom or a group removable during a coupling reaction; and Cp1 and Cp2 are the same or different, each representing an aromatic condensed heterocyclic or aromatic condensed hydrocarbon residue having at least a phenolic hydroxyl group and optionally having a substituted carbamoyl group or a heterocyclic group, thereby producing a bisazo compound of the general formula (I):

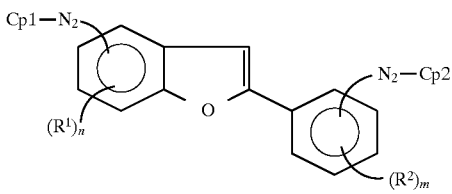

wherein $R^1$, $R^2$, n, m, Cp1 and Cp2 each have the same definition as described above.

In accordance with a fourth aspect of the present invention, there is provided a 2-(nitrobenzyloxy) nitrobenzaldehyde derivative of the general formula (IV):

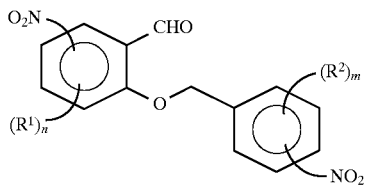

wherein $R^1$, $R^2$, n and m each have the same definition as in the general formula (I).

In accordance with a fifth aspect of the present invention, there is provided a 2-(nitrophenyl) nitrobenzo[b]furan derivative of the general formula (V):

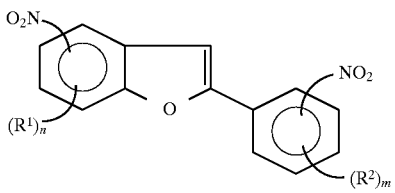

wherein $R^1$, $R^2$, n and m each have the same definition as in the general formula (I).

In accordance with a sixth aspect of the present invention, there is provided a 2-(aminophenyl) aminobenzo[b]furan derivative of the general formula (VI):

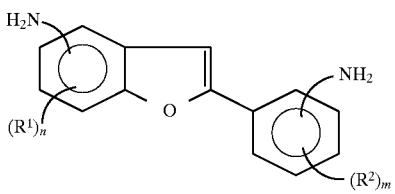

wherein $R^1$, $R^2$, n and m each have the same definition as in the general formula (I).

DESCRIPTION OF THE PREFERRED EMBODIMENTS

Figure 1:
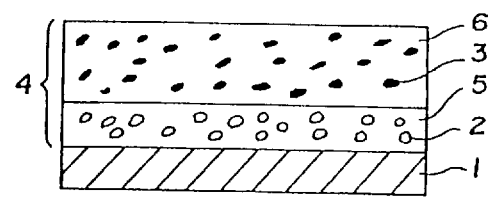
FIGS. 1 to 6 are sectional views schematically illustrating the layer structures of electrophotographic photoconductors each using a bisazo compound of the present invention.

There will hereinafter be described the bisazo compounds of the general formulae (I) and (I)' and the intermediate compounds (IV), (V) and (VI) according to the present invention.

In the above general formulae, $R^1$ and $R^2$ are the same or different, each representing a hydrogen atom, a halogen atom, a lower alkyl group, an aralkyl group optionally having a substituent, a lower alkoxy group, a di-(lower alkyl) amino group having 4 to 12 carbons, or a trifluoromethyl group.

Examples of the halogen atom include a fluorine atom, a chlorine atom and a bromine atom.

The lower alkyl group may be either linear or branched, and is a $C_{1-4}$ alkyl group. More specific examples thereof include methyl, ethyl, n-propyl, iso-propyl, n-butyl, iso-butyl, sec-butyl, and tert-butyl.

The lower alkoxy group may be either linear or branched, and is a $C_{1-4}$ alkoxy group. More specific examples thereof include methoxy, ethoxy, n-propoxy, iso-propoxy, n-butoxy, sec-butoxy, and tert-butoxy.

The di-(lower alkyl)amino group is a di-($C_{2-6}$ alkyl)amino group. More specific examples thereof include dimethylamino, diethylamino, ethylmethylamino, di-iso-propylamino, and di-n-butylamino.

The aralkyl group is a phenyl-$C_{1-3}$ alkyl group, and examples thereof include benzyl and phenethyl.

Examples of the optional substituent for the aralkyl group include lower alkyl groups such as methyl and ethyl, lower alkoxy groups such as methoxy and ethoxy, substituted amino groups such as methylamino, dimethylamino, ethylamino, ethylmethylamino and diethylamino, and halogen atoms such as fluorine atom, chlorine atom and bromine atom. The aralkyl group may have any of these substituents either alone or in combination.

The number n represents an integer from 1 to 3 and, if n is two or greater, the groups $R^1$ may be the same or different. The number m represents an integer from 1 to 4 and, if m is two or greater, the groups $R^2$ may be the same or different. If neither $R^1$ nor $R^2$ is a hydrogen atom, n and m are preferably 1.

In the above general formulae, $R^1$ and $R^2$ more preferably each represent a hydrogen atom, a chlorine atom, a methyl group, a methoxy group, an ethoxy group, or a trifluoromethyl group.

In the above general formulae (I) and (I)', Cp1 and Cp2 are the same or different, each representing an aromatic condensed heterocyclic or aromatic condensed hydrocarbon residue having at least a phenolic hydroxyl group and optionally having a substituted carbamoyl group or a heterocyclic group. More specific examples thereof include those represented by the following general formulae (VII-1) to (VII-6):

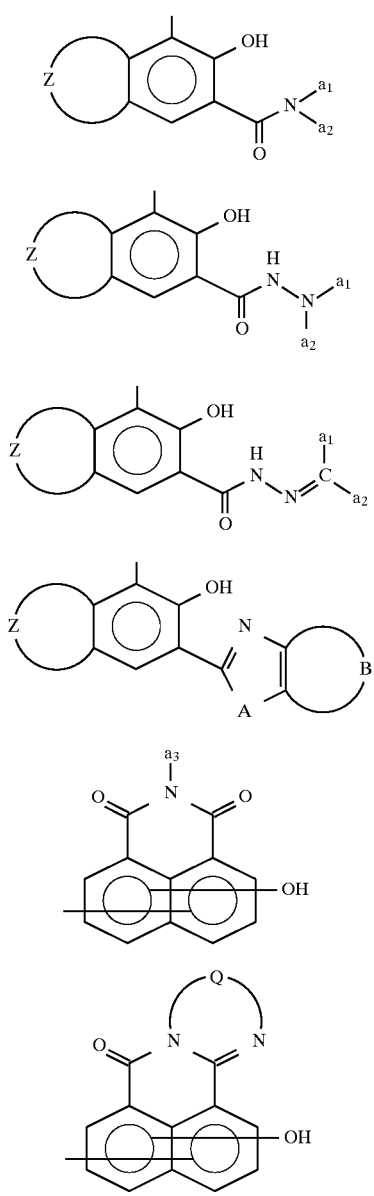

wherein Z is an atomic group which is required for formation of an aromatic polycyclic group such as a naphthalene ring or anthracene ring resulting from condensation with a benzene ring, or an aromatic heterocyclic group such as a carbazole ring, dibenzocarbazole ring, dibenzofuran ring or fluorene ring resulting from condensation with a benzene ring; Q is a divalent linear hydrocarbon group or aromatic hydrocarbon group required for formation of a five-membered ring or a six-membered ring, or a divalent aromatic heterocyclic group having a nitrogen atom in its ring; A is an oxygen atom, a sulfur atom, or an N-a4 group (wherein a4 is a hydrogen atom, or a lower alkyl group, an aromatic hydrocarbon group or a lower aralkyl group optionally having a substituent); B is a divalent residue required for formation of an aromatic hydrocarbon group by condensation with a carbon double bond; a1 and a2 are independent, each representing a hydrogen atom (excluding a case where a1 and a2 are both hydrogen atoms), or a lower alkyl group, an aromatic hydrocarbon group, an aralkyl group or an aromatic heterocyclic group, optionally having a substituent; a3 is a lower alkyl group, an aromatic hydrocarbon group, an aralkyl group or an aromatic heterocyclic group, optionally having a substituent.

Examples of the atomic group for the group Z include residues such as derived from benzene, naphthalene and carbazole.

Examples of the divalent linear hydrocarbon group for the group Q include methylene, ethylene and trimethylene. Examples of the divalent aromatic hydrocarbon group for the group Q include phenylene and naphthylene.

Examples of the lower alkyl group and the aralkyl group for the groups a1 and a2 include those employed for the groups $R^1$ and $R^2$.

The aromatic hydrocarbon groups for the groups a1 and a2 are $C_{6-14}$ aromatic hydrocarbon residues, and examples thereof include phenyl, naphthyl and anthracenyl.

Examples of the aromatic heterocyclic groups for the groups a1 and a2 include furyl, pyridyl, phenethyl, carbazolyl, dibenzofuryl and benzoxazolyl.

Examples of the optional substituent for the alkyl group, the aralkyl group, the aromatic hydrocarbon group and the aromatic heterocyclic group for the groups a1 and a2 include halogen atoms such as chlorine atom, fluorine atom and bromine atom, lower alkyl groups such as methyl, ethyl, propyl, isopropyl, n-butyl, s-butyl and t-butyl, alkoxy groups such as methoxy, ethoxy, propoxy, butoxy and phenoxybenzyloxy, a nitro group, a cyano group, and substituted amino groups such as dimethylamino, dibenzylamino, diphenylamino, morpholyno and piperidino. The aforesaid groups for the groups a1 and a2 may each have any of these substituents either alone or in combination.

Examples of the alkyl group, the aralkyl group, the aromatic hydrocarbon group and the aromatic heterocyclic group for the group a3 each optionally having a substituent include those employed for the groups a1 and s2.

Examples of the divalent residue required for formation of an aromatic hydrocarbon group by condensation with a carbon double bond for the group B include residues such as derived from benzene, naphthalene and carbazole.

More preferably, the group Z is a residue derived from benzene, naphthalene or carbazole; the group Q is phenylene; the groups a1 and a2 are a hydrogen atom, chlorophenyl, trifluorophenyl, tolyl or ethylphenyl; the group a3 is di-or tri-fluorophenyl; the group A is an oxygen atom or a sulfur atom; and the group B is phenylene.

Among the above bisazo compounds, preferable ones are represented by the general formula (I)':

$$\text{Cp1}-\text{N}_2 \cdots (R^1)_n \cdots O \cdots (R^2)_m \cdots N_2-\text{Cp2} \quad (I)'$$

wherein $R^1$, $R^2$, n, m, Cp1 and Cp2 each have the same definition as in the general formula (I).

The 2-(nitrophenyl)-nitrobenzo[b]furan derivatives, the 2-(aminophenyl)-aminobenzo[b]furan derivatives and the bisazo compounds of the present invention can readily be synthesized through the following scheme.

The 2-(nitrophenyl)-nitrobenzo[b]furan derivative can be synthesized in a single step by heating a mixture consisting of a nitrosalicylaldehyde derivative of the general formula (II):

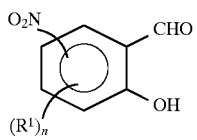

wherein $R^1$ and n each have the same definition as in the general formula (I) and a nitrobenzyl halide derivative of the general formula (III):

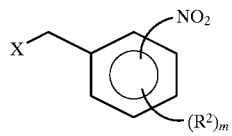

wherein X is a halogen atom such as chlorine atom or bromine atom in a molar ratio of 1:1 to 1:1.3 in a solvent in the presence of an organic amine base (condensing agent) added thereto in a molar ratio of 2:1 to 5:1 with respect to the nitrobenzyl halide derivative.

Examples of the solvent to be used include tetrahydrofuran, 1,4-dioxane, ethyleneglycol, dimethyl ether, N,N-dimethylformamide and N,N-dimethylacetamide.

Examples of the organic amine base include triethylamine, N,N-diisopropylethylamine, 1,5-diazabicyclo[4.3.0]nona-5-ene and 1,8-diazabicyclo[5.4.0]undeca-7-ene.

Alternatively, the 2-(nitrophenyl)nitrobenzo [b]furan derivative may be synthesized stepwise. More specifically, a mixture consisting of a nitrosalicylaldehyde derivative and a nitrobenzyl halide derivative in a molar ratio of 1:1 to 1.5:1 is heated to provide an intermediate product of a 2-(nitrobenzyloxy)nitrobenzaldehyde derivative of the general formula (IV), which is once isolated. Then, a mixture consisting of the 2-(nitrobenzyloxy) nitrobenzaldehyde derivative and the organic amine base in a molar ratio of 1:1 to 2.5:1 is heated in a solvent to provide the 2-(nitrophenyl) nitrobenzo[b]furan derivative of the general formula (V).

In turn, a mixture consisting of 100- to 200-mesh iron powder and the 2-(nitrophenyl)nitrobenzo [b]furan derivative in a molar ratio of 1:20 to 1:40 is heated in a solvent mixture with stirring for reduction. Thus, a 2-(aminophenyl) aminobenzo[b]furan derivative of the general formula (VI) is synthesized.

Examples of the solvent mixture include tetrahydrofuran/water and 1,4-dioxane/water.

Subsequently, the 2-(aminophenyl)aminobenzo[b]furan derivative is tetra-azotized by an ordinary method. The obtained tetraazo compound is, as required, isolated as a borofluoride, a zinc chloride double salt or the like, and then coupled with couplers Cp1-Y and Cp2-Y wherein Y is a hydrogen atom or a group removable during the coupling reaction; Cp1 and Cp2 each have the same definition as in the general formula (I) in a polar organic solvent or an aqueous solution in the presence of a basic catalyst. Thus, the bisazo compound of the general formula (I):

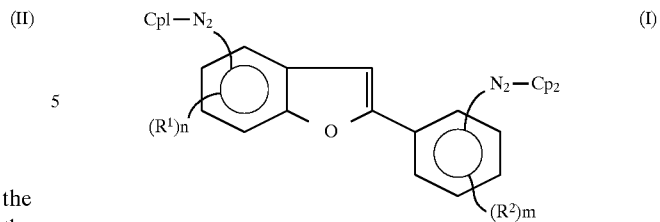

($R^1$, $R^2$, n, m, Cp1 and Cp2 each have the same definition as described above) can readily be synthesized.

Examples of the polar organic solvent include N,N-dimethylformamide, dimethyl sulfoxide, ethanol and dioxane.

Examples of the basic catalyst include sodium hydroxide, potassium hydroxide, sodium acetate, pyridine, triethylamine and triethanolamine.

The bisazo compound of the present invention may be synthesized with a high yield through the reaction scheme described above.

In accordance with the present invention, the bisazo compound of the general formula (I) is used as a charge carrier generating substance for an electrophotographic photoconductor. In combination therewith, any other known charge carrier generating substances may be used for the electrophotographic conductor of the present invention. Examples of specific known charge carrier generating substances include: phthalocyanine pigments such as various metal phthalocyanines, a metal-free phthalocyanine, and halogenated metal-free phthalocyanines; perylene pigments such as peryleneimide and perylenic anhydride; azo pigments such as bisazo pigments and trisazo pigments; quinacridone pigments; anthraquinone pigments; triphenylmethane dyes such as Methyl Violet, Crystal Violet, Knight Blue and Victoria Blue; acridine dyes such as erythrosine, Rhodamine B, Rhodamine 3R, Acridine Orange and Frapeocine; thiazine dyes such as Methylene Blue and Methylene Green; cyanin dyes; styryl dyes; pyrylium salt dyes; and thiopyrylium salt dyes.

The intermediate products of the general formulae (IV) to (VI) are used as materials for a charge carrier transferring substance of an electrophotographic photoconductor.

A charge carrier transferring substance resulting from the intermediate products of the general formulae (IV) to (VI) will next be described.

The charge carrier transferring substance resulting from the intermediate products of the present invention is a diamine compound of the general formula (VIII):

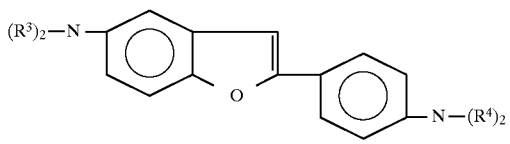

wherein $R^3$ and $R^4$ are the same or different, each representing an aryl group, an aralkyl group or a vinylidene group optionally having a substituent.

The charge carrier transferring substance can be readily produced by subjecting the intermediate product of the general formula (VI) to:

(1) Tetraarylation by the Ullmann reaction;
(2) Bisarylation by the Ullmann reaction, and then aralkylation with an aralkyl halide; or
(3) Bisarylation by the Ullmann reaction, and then bisvinylidenation by dehydration condensation with an α, α-di-substituted acetaldehyde derivative.

The electrophotographic photoconductor is produced by forming a photosensitive layer on a conductive support base. The photosensitive layer of the electrophotographic photoconductor according to the present invention may be of any of various known forms. Exemplary forms of the photosensitive layer are:

(1) A photosensitive layer comprising a bisazo compound alone;

(2) A photosensitive layer comprising a binder and a bisazo compound dispersed therein; and (3) A photosensitive layer comprising a charge carrier transferring substance and a bisazo compound dispersed therein.

The photosensitive layer is employed as a charge carrier generating layer, and a charge carrier transferring layer containing a charge carrier transferring substance is formed thereon.

The photosensitive layer contains one or more of the bisazo compounds of the present invention and, when absorbed light, generates charge carriers at a very high efficiency. Migration of the generated charge carriers within the photosensitive layer may be achieved with the bisazo compound used as a transfer medium, but preferably with the charge carrier transferring substance used as the transfer medium. From this view point, the aforesaid forms (1) and (2) of the photosensitive layer are particularly preferred.

The support base having the photosensitive layer formed thereon serves for migration of charge carriers (electrons or holes) generated in the photosensitive layer by light absorption when an electric field is applied to the photosensitive layer. Examples of the conductive support base include a metal drum, a metal sheet, and a metal laminate and a metal deposition film formed on the drum or the sheet, and a plastic film, a plastic drum and a paper sheet which are imparted with a conductivity by applying thereon a coating liquid containing a conductive material and a binder. Examples of specific metals usable for the conductive support base include copper and aluminum. Examples of the conductive material include powdery metals, carbon black, copper iodide and polymeric electrolytes.

The photosensitive layer on which a latent image (electrostatic latent image) is to be formed by two-dimensional electrostatic charge distribution comprises of a charge carrier generating substance and a charge carrier transferring substance as essential substances, and optionally contains a binder, a sensitizer, a plasticizer, an electric-characteristics deterioration preventive agent, an antioxidant and a leveling agent.

It is preferred to use as the charge carrier transferring substance a compound produced from the aforesaid intermediate produces of the present invention, because the production process therefor is simple. Besides the aforesaid compound, known charge carrier transferring substance may be used. There are two types of charge carrier transferring substances, i.e., electron transferring substances and hole transferring substances. Either of these two types of charge carrier transferring substances can be used for the photosensitive layer of the photoconductor. Alternatively, a mixture of charge carrier transferring substances of the same type may be used.

Usable as the electron transferring substances are electron attractive compounds having electron attractive groups such as nitro group, cyano group and ester group. Examples thereof include nitrofluorenone derivatives such as 2,4,7-trinitrofluorenone and 2,4, 5,7-tetranitrofluorenone, tetracyanoquinodimethane, tetracyanoethylene, 2,4,5,7-tetranitroxanthone and 2,4,8-trinitrothioxanthone, and polymers of these electron attractive compounds.

Usable as the hole transferring substances are organic electron-donative electrophotoconductive compounds. Examples thereof include heterocyclic compounds such as carbazole, indole, imidazole, oxazole, thiazole, oxadiazole, pyrazole, pyrazoline, thiadiazole; triarylalkane compounds such as triphenylmethane; triarylamine compounds such as 4-methoxy-4'-(4-methoxystyryl)triphenylamine, 4-methoxy-4'-styryltriphenylamine; phenylenediamine compounds; N-phenylcarbazole compounds; stilbene compounds such as β-phenyl-[4-(benzylamino)]stilbene and β-phenyl-[4-(N-ethyl-N-phenylamino)]stilbene; hydrazone compounds such as 4-(dibenzylamino)benzaldehyde-N,N-diphenylhydrazone, 4-(ethylphenylamino)benzaldehyde-N,N-diphenylhydrazone, 3,3-bis(4'-diethylaminophenyl)acrolein-N,N-diphenylhydrazone; and enamine compounds. Compounds substituted with electron donative groups such as a substituted amino group (e.g., a dialkylamino group, a diphenylamino group), an alkyl group and alkoxy group and compounds substituted with an aromatic hydrocarbon group substituted with any of these electron donative groups have a high electron-donative ability and are particularly useful.

Examples of specific polymeric hole transferring compounds include poly-N-vinylcarbazole, halogenated poly-N-vinylcarbazole, polyvinylpyrene, polyvinylanthracene, polyvinylacridine and polyglycidylcarbazole.

Among the aforesaid hole transferring substances, a compound having an enamine molecular structure offers a high hole migration speed.

The charge carrier transferring substance is not limited to those described above. These charge carrier transferring substances may be used either alone or in combination.

The electrophotographic photoconductor can be produced by an ordinary method.

More specifically, the production of the electrophotographic photoconductor of the form (1) is achieved by applying on the conductive support base a coating liquid containing the bisazo compound of the general formula (I) of the present invention dissolved or dispersed in a suitable solvent and drying the applied coating liquid to form a photosensitive layer typically having a thickness of 0.1 μm to several dozens of micrometers.

Examples of the solvent to be used for preparation of the coating liquid include basic solvents such as n-butylamine and ethylenediamine capable of dissolving therein an azo compound; ethers such as tetrahydrofuran, 1, 4-dioxane and ethylene glycol monomethyl ether; ketones such as acetone, methyl ethyl ketone and cyclohexanone; aprotic polar solvents such as N,N-dimethylformamide, N,N-dimethylacetamide, acetonitrile, N-methylpyrrolidone and dimethyl sulfoxide; aromatic hydrocarbons such as toluene, benzene, xylene, chlorobenzene and dichlorobenzene; halogenated hydrocarbons such as dichloromethane, dichloroethane, chloroform, dichloroethylene and tetrachloromethane; alcohols such as methanol, ethanol and isopropanol; and esters such as methyl acetate, ethyl acetate and methyl cellosolve acetate. These solvents may be used either alone or in combination.

Exemplary coating methods to be employed include dip coating, spray coating, spinner coating, bead coating, Meyer bar coating, blade coating, roller coating and curtain coating.

For the production of an electrophotographic photoconductor having a photosensitive layer of the form (2), a binder is dissolved in the coating liquid to be used for formation of the photosensitive layer of the form (1). In this case, the solvent for the coating liquid is preferably capable of dissolving the binder.

The binder may be selected from a variety of insulative resins. Preferable examples thereof include polymers and copolymers of vinyl compounds such as styrene, vinyl acetate, acrylates and methacrylates, resins such as phenoxy resins, polysulfones, acrylate resins, polycarbonates, polyesters, cellulose esters, cellulose ethers, butyral resins, epoxy resins and acrylpolyol resins. The amount of the binder to be used is 0.1 to 20 times, preferably 0.1 to 5 times the weight of the bisazo compound.

For production of an electrophotographic photoconductor having a photosensitive layer of the form (3), a charge carrier transferring substance may be dissolved in the coating liquid to be used for the formation of the photosensitive layer of the form (1).

Any of the charge carrier transferring substances described above may be used. In this case, a binder is preferably added to the coating liquid unless a charge carrier transferring substance such as poly-N-vinylcarbazole or polyglycidylcarbazole which itself serves as a binder is used. The amount of the binder to be used is typically 0.5 to 100 times, preferably 0.3 to 1.2 times the weight of the bisazo compound. Where the charge carrier transferring substance doubling as a binder is to be used, the amount thereof is preferably 1 to 10 times the weight of the bisazo compound.

The charge carrier transferring layer is formed on the photosensitive layer of the form (1) to (3) by applying thereon a coating liquid containing the charge carrier transferring substance dissolved or dispersed in a suitable solvent and drying the applied coating liquid. Thus, the electrophotographic photoconductor can be produced which has the photosensitive layer of lamination type. In this case, the photosensitive layer of the form (1) to (3) serves as a charge carrier generating layer. The charge carrier transferring layer is not necessarily formed on top of the charge carrier generating layer, but may be provided between the charge carrier generating layer and the conductive support base. However, the former case is more preferred in terms of durability.

The formation of the charge carrier transporting layer is achieved in substantially the same manner as for the formation of the photosensitive layer of the form (3), except that the coating liquid to be used does not contain the bisazo compound. The charge carrier transferring layer typically has a thickness of 5 $\mu$m to 50 $\mu$m.

The photosensitive layer of the electrophotographic photoconductor of the present invention may contain a known sensitizer. Preferably used as the sensitizer are organic electrophotoconductive substances, inorganic electrophotoconductive substances, Lewis acids and dyes capable of forming charge transferring complexes, and the like.

Examples of specific organic electrophotoconductive substances include copper-phthalocyanine pigments and perylene pigments. Examples of specific inorganic electrophotoconductive substances include selenium and selenium-arsenic alloys. Examples of specific Lewis acids include quinones such as chloranil, 2,3-dichloro-1,4-naphthoquinone, 2-methylanthraquinone, 1-nitroanthraquinone, 1-chloro-5-nitroanthraquinone, 2-chloroanthraquinone; aldehydes such as 4-nitrobenzaldehyde; ketones such as 9-benzoylanthracene, indandione, 3,5-dinitrobenzophenone, 3,3',5,5'-tetranitrobenzophenone; phthalic anhydride and 4-chloronaphthalic anhydride; cyano compounds such as tetracyanoethylene, terephthalmalondinitrile, 4-nitrobenzalmalonitrile; and phthalides such as 3-benzalphthalide and 3-($\alpha$-cyano-p-chlorobenzal) phthalide, which are electron attractive compounds.

Examples of specific dyes include triphenylmethane dyes such as Methyl Violet, Brilliant Green and Crystal Violet; acridine dyes such as erythrosine, Rhodamine B, Rhodamine 3R, Acridine Orange, Frapeocine; thiazine dyes such as Methylene Blue; oxazine dyes such as Capri Blue and Meldora Blue; quinone dyes such as quinizarin; and cyanin dyes, styryl dyes, pyrylium dyes, thiopyrylium dyes and benzopyrylium dyes. These dyes may be used alone, but are often used along with any of the aforesaid pigments to increase the efficiency of the charge carrier generation.

The photosensitive layer of the electrophotographic photoconductor of the present invention may contain a plasticizer for facilitating the film formation and improving the mechanical strength.

Examples of specific plasticizers include phthalates (e.g., DOP, DBP and the like), phosphates (e.g., TCP, TOP and the like), adipates, nitrile rubber, epoxy compounds, chlorinated paraffin, chlorinated aliphatic esters, and aromatic compounds such as alkylated naphthalene.

The photosensitive layer may, as required, contain additives such as an electric-characteristics deterioration preventive agent, an anti-oxidant and a leveling agent.

The electric-characteristics deterioration preventive agent prevents the increase in the residual potential and the reduction in the charge potential and the photosensitivity, which would occur through repetitive use of the electrophotographic photoconductor.

Examples of the electric-characteristics deterioration preventive agent include electron attractive compounds such as tribenzylamine, tetrabenzyl-p-xylenediamine, 1-chloroanthraquinone, benzoquinone, 2,3-dichloronaphthoquinone, naphthoquinone, 4,4'-dinitrobenzophenone, 4,4'-dichlorobenzophenone, 4-nitrobenzophenone, 4-nitrobenzalmalondinitrile, $\alpha$-cyano-$\beta$-(p-cyanophenyl)ethyl acrylate, 9-anthracenylmethylmalondinitrile, 1-cyano-1-(p-nitrophenyl)-2-(p-chlorophenyl)ethylene, and 2,7-dinitrofluorenone.

Examples of the anti-oxidant include BHT and BHQ. Examples of the leveling agent include silicon oil and the like.

The photosensitive layer of the electrophotographic photoconductor of the present invention may optionally have an adhesive layer, an intermediate layer, an insulative photoconductive layer and a surface protective layer. The constructions of exemplary electrophotographic photoconductors optionally having an intermediate layer and a surface protective layer will be described with reference to FIGS. 1 to 6.

(1) In FIG. 1, there is shown a function-separated electrophotographic photoconductor which comprises a laminate photosensitive layer 4 formed on a conductive support base 1 and having a charge carrier generating layer 5 containing as a principal component a charge carrier generating substance dispersed in a binder and a charge carrier transferring layer 6 containing as a principal component a charge carrier transferring substance 3 dispersed in a binder. Used as the charge carrier generating substance 2 in the charge carrier generating layer 5 is the bisazo compound of the present invention.

Figure 2:
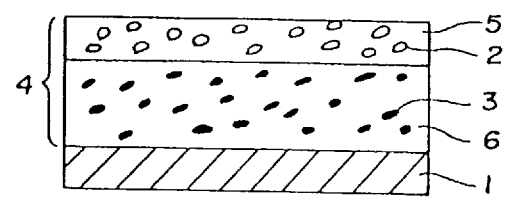

(2) In FIG. 2, there is shown another function-separated electrophotographic photoconductor which comprises a laminate photosensitive layer having a charge carrier generating layer 5 and a charge carrier transferring layer 6 like the electrophotographic photoconductor shown in FIG. 1. However, the charge carrier generating layer 5 is formed on a surface of the charge carrier transferring layer 6. Used as the charge carrier generating substance 2 in the charge carrier generating layer 5 is the bisazo compound of the present invention.

Figure 3:
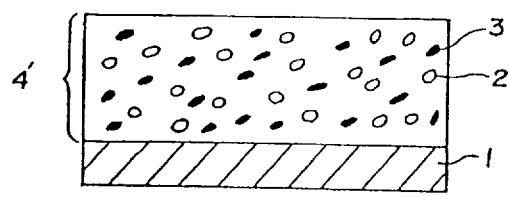

(3) In FIG. 3, there is shown further another electrophotographic photoconductor which comprises a photosensitive layer 4' of single-layer structure formed on a conductive support base 1 and containing a charge carrier generating substance 2 and a charge carrier transferring substance 3 dispersed in a binder.

Figure 4:
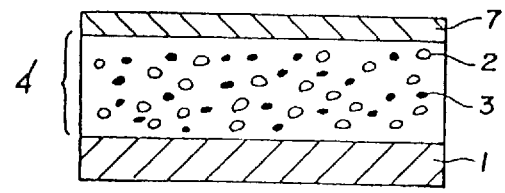

(4) In FIG. 4, there is shown still another electrophotographic photoconductor which comprises a photosensitive layer 4' having the same construction as shown in FIG. 3 and a surface protective layer 7 formed thereon.

Figure 5:
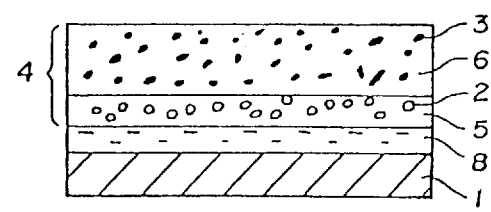

(5) In FIG. 5, there is shown yet another function-separated electrophotographic photoconductor which comprises a conductive support base 1, a photosensitive layer 4 having the same construction as shown in FIG. 1, and an intermediate layer 8 provided therebetween.

Figure 6:
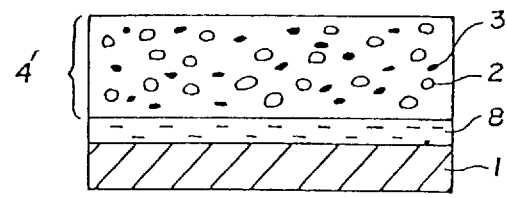

(6) In FIG. 6, there is shown still another electrophotographic photoconductor which comprises a conductive support base 1, a photosensitive layer 4' of a single-layer structure having the same construction as shown in FIG. 3, and an intermediate layer 8 provided therebetween.

The surface protective layer 7 provided on the surface of the photosensitive layer 4' serves to improve the durability against a mechanical stress, and to receive and retain electric charge generated by corona discharge in a dark place. Therefore, the surface protective layer 7 should be formed of a chemically stable material and should be pervious to light which is to be sensed by the charge carrier generating layer. When the electrophotographic photoconductor is exposed to light, the surface protective layer allows the light to reach the charge carrier generating layer, and receives generated charge to neutralize its surface charge. Further, the surface protective layer should be as transparent as possible in a wavelength region in which light absorbance of the charge carrier generating substance is the maximum.

Examples of specific materials having such properties include organic insulative film formation materials such as acrylic resins, polyaryl resins, polycarbonate resins and urethane resins (which are to be used either alone or in combination with a low resistance compound such as tin oxide or indium oxide dispersed therein), acryl-modified silicone resins, epoxy-modified silicone resins, alkyd-modified silicone resins, polyester-modified silicone resins, urethane-modified silicone resins and other silicone resins as hard coating materials (which are to be used either alone or as a mixture thereof containing silicon oxide, titanium oxide, indium oxide or zirconium oxide as a principal component along with condensation products with a film-formable metal alkoxy compound for improvement of the durability). Plasma-polymerized films can also be used which may optionally contain oxygen, nitrogen, halogen, a Group III element or a Group V element. Alternatively, the surface protective film may be formed of a metal or a metal oxide by vapor deposition or sputtering.

The intermediate layer 8 provided between the conductive support base 1 and the photosensitive layer 4 or 4' may be imparted with a protective function and an adhesive function. Further, the intermediate layer 8 may be adapted for improvement of the coatability or improvement of the efficiency of charge injection into the photosensitive layer. Examples of specific materials for the intermediate layer 8 include casein, polyvinyl butyral, polyvinyl alcohol, nitrocellulose, ethylene-acrylic acid copolymer, polyamides (Nylon 6, Nylon 66, Nylon 610, nylon copolymers, alkoxymethyl nylons and the like), polyurethane, gelatin and aluminum oxide.

EXAMPLES

The present invention will hereinafter be described by way of examples thereof. It should be noted that the scope of the invention be not limited by these examples.

Synthesis Example 1

Synthesis of 2-(p-aminophenyl)5-aminobenzo [b] furan 10.0 g (1.0 equivalent) of 5-nitrosalicylaldehyde and 13.3 g (1.03 equivalents) of p-nitrobenzyl bromide were dissolved in 45 ml of 1,4-dioxane, and then 12.5 g (1.2 equivalents) of N,N-diisopropylethylamine was added thereto. The mixture was heated at about 100° C. for two hours with stirring, and then cooled to room temperature. Thereafter, the resulting solid substance was filtered off and sufficiently washed with ethanol. Thus, 16.74 g of a product was obtained.

The product was analyzed by way of $^{13}$C-NMR. The results are as follows.

Normal $^{13}$C-NMR (d-DMSO): 69.69 (OCH$_2$), 115.01 (CH), 123.66 (CH), 123.90 (CH), 124.35 (C), 128.26 (CH), 130.80 (CH), 141.18 (C), 143.29 (C), 147.23 (C), 163.97 (C), 187.96 (CHO).

DEPT135 $^{13}$C-NMR (d-DMSO): 69.69, 115.01, 123.66, 123.90, 128.26, 130.80.

The product was identified as 2-(p-nitrobenzyloxy-5-nitrobenzaldehyde by the $^{13}$C-NMR analysis. The yield was 92.7%.

Figure 7:
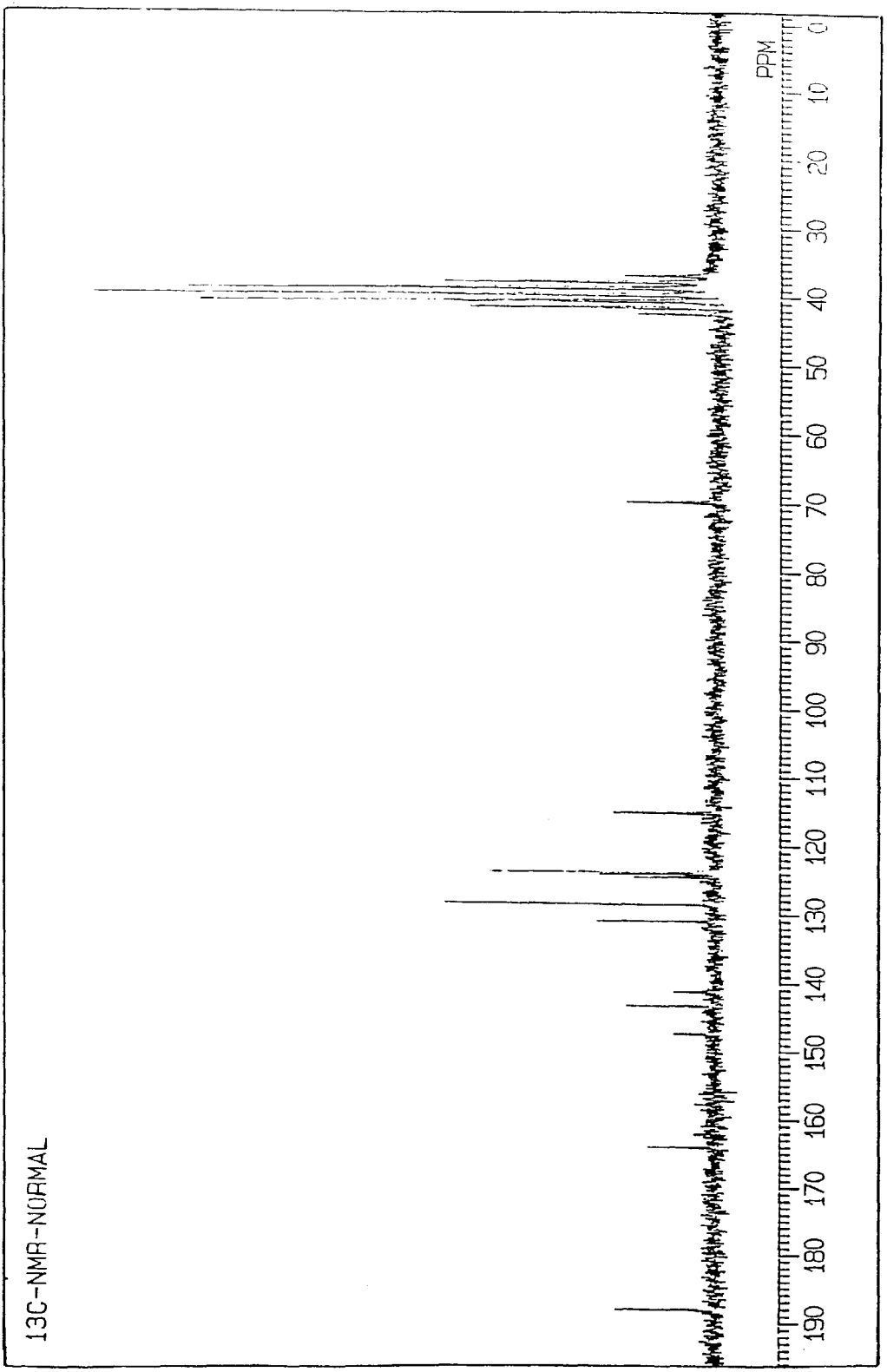
FIG. 7 is a chart of normal $^{13}$C-NMR spectrum of 2-(p-nitrobenzyloxy)-5-nitrobenzaldehyde of the present invention.
Figure 8:
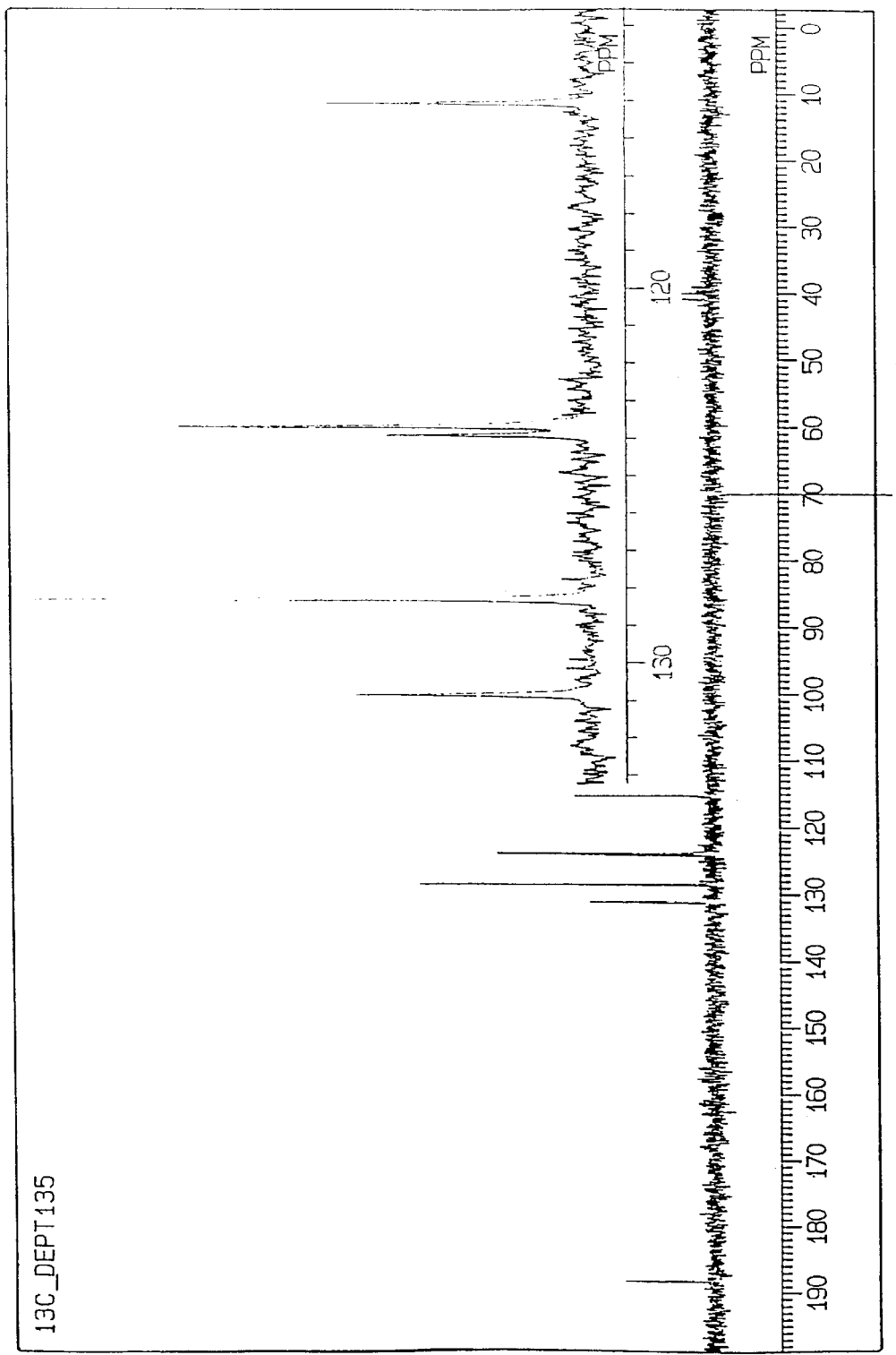
FIG. 8 is a chart of DEPO-135 $^{13}$C-NMR spectrum of 2-(p-nitrobenzyloxy)-5-nitrobenzaldehyde of the present invention.

It is noted that FIGS. 7 and 8 are the charts of the normal $^{13}$C-NMR and the DEPT135 $^{13}$C-NMR, respectively, of 2-(p-nitrobenzyloxy)-5-nitrobenzaldehyde.

In turn, 16.09 g (1.0 equivalent) of 2-(p-nitrobenzyloxy)-5-nitrobenzaldehyde thus obtained was dissolved in 50 ml of 1,4-dioxane, and then 9.7 g (1.3 equivalents) of 1,8-diazabicyclo[5.4.0]undeca-7-ene was added thereto. The resulting mixture was heated at about 100° C. for three hours with stirring, and then cooled to room temperature. Thereafter, the resulting solid substance was filtered off and sufficiently washed with ethanol. Thus, 12.42 g of 2-(p-nitrophenyl)-5-nitrobenzo [b]furan was obtained (yield: 82%).

42 g (1.0 equivalent) of 2-(p-nitrophenyl)-5-nitrobenzo [b]furan was added to 150 ml of a solvent mixture containing 1,4-dioxane and water in a ratio of 1:1 and 48.85 g (20.0 equivalents) of 100-mesh iron powder preliminarily activated with 0.5 ml of concentrated hydrochloric acid, and the resulting mixture was heated at about 110° C. for two hours under reflux with vigorous stirring. Immediately after the completion of the reaction was confirmed by way of TLC (thin-layer chromatography), the supernatant of the resulting reaction mixture was filtered in a hot state through a Celite filter. The residue was sufficiently washed with hot 1,4-dioxane and filtered away. After this filtration process was repeated three or four times, the filtrates were put together and concentrated by means of an evaporator. Thereafter, the resulting product was recrystallized from ethanol. Thus, 7.1 g of an orange product was obtained.

The product was analyzed by way of $^{13}$C-NMR. The results are as follows. Normal $^{13}$C-NMR (d-DMSO): 97.35 (CH), 103.50 (CH), 110.33 (CH), 111.46 (CH), 113.79 (CH), 117.82 (C), 125.66 (CH), 130.05 (C), 144.40 (C), 147.12 (C), 149.29 (C), 156.54 (C).

DEPT135 $^3$C-NMR (d-DMSO): 97.35, 103.50, 110.33, 111.46, 113.79, 125.66.

The product was identified as 2-(p-aminophenyl)-5-aminobenzo[b]furan by the $^{13}$C-NMR analysis. The yield was 90%.

Figure 9:
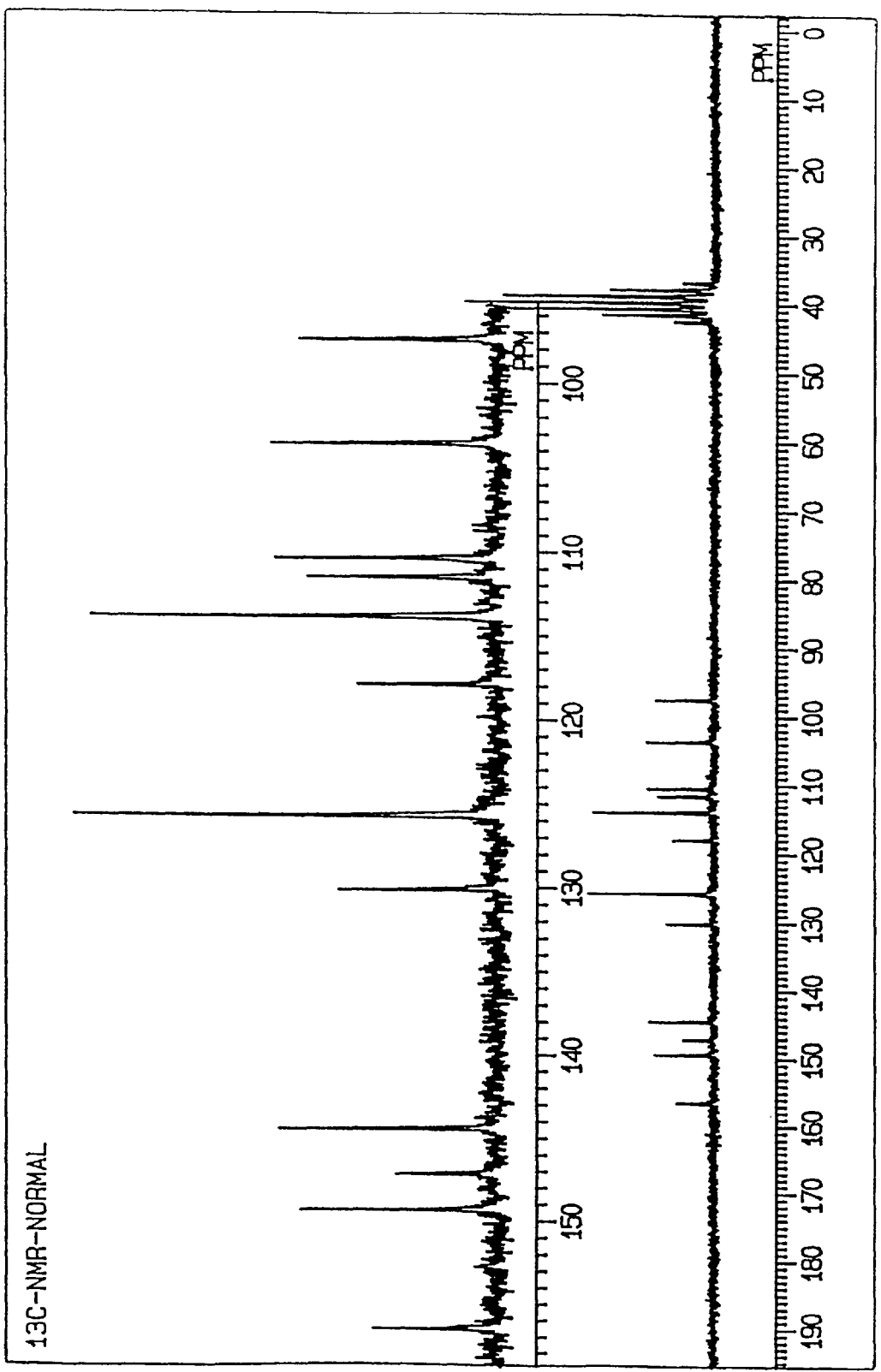
FIG. 9 is a chart of normal $^{13}$C-NMR spectrum of 2-(p-aminophenyl)-5-aminobenzo[b]furan of the present invention.
Figure 10:
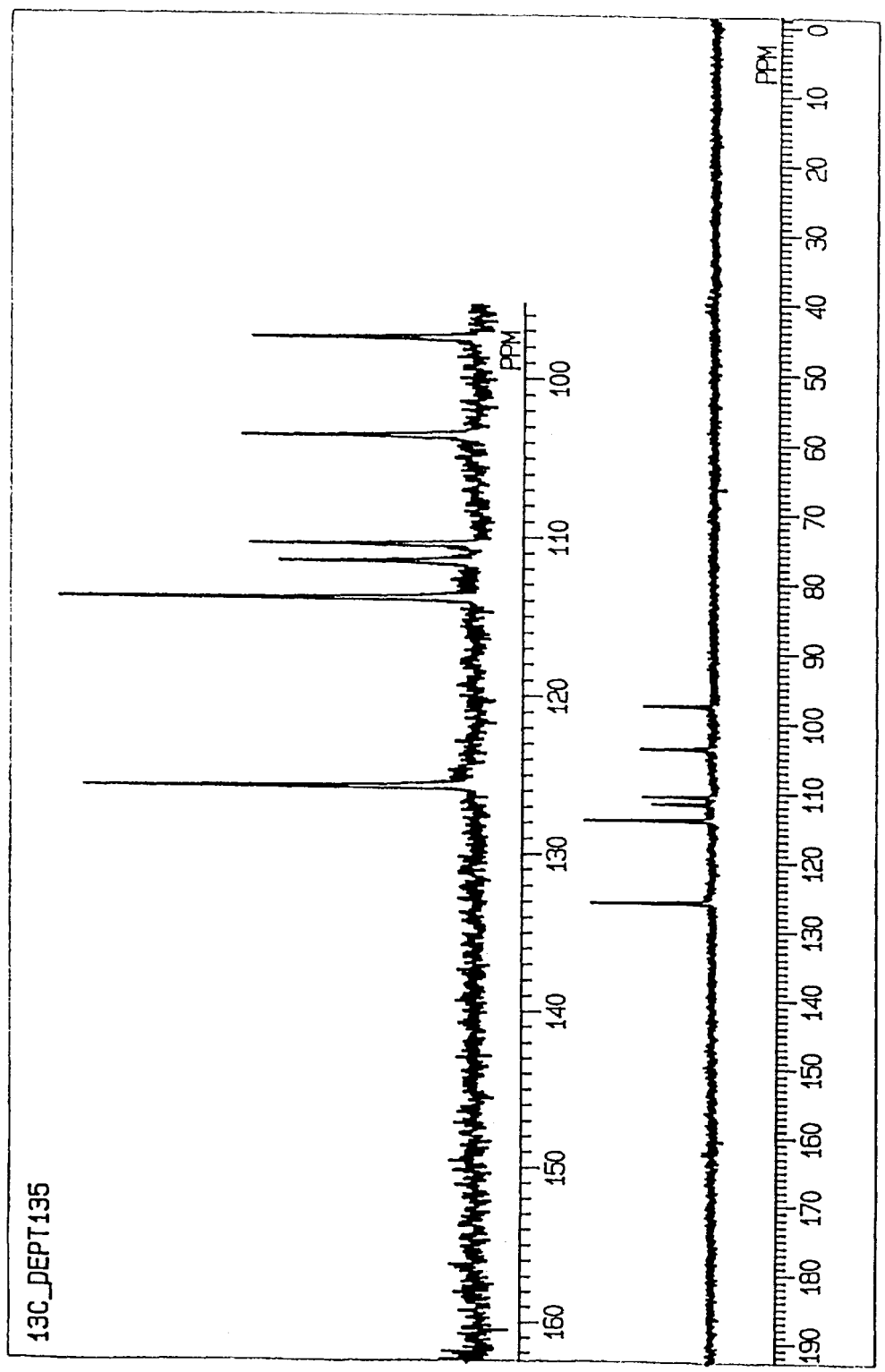
FIG. 10 is a chart of DEPO-135 $^{13}$C-NMR spectrum of 2-(p-aminophenyl)-5-aminobenzo[b]furan of the present invention.

It is noted that FIGS. 9 and 10 are charts of the normal $^{13}$C-NMR and the DEPT135 $^3$C-NMR, respectively, of 2-(p-aminophenyl)-5-aminobenzo[b]furan.

Synthesis Example 2

Synthesis of 2-(p-aminophenyl)5-amino-7-methoxybenzo[b]furan 5.0 g (1.0 equivalent) of 3-methoxy-5-nitrosalicylaldehyde and 6.03 g (1.1 equivalents) of p-nitrobenzyl bromide were dissolved in 15 ml of 1,4-dioxane, and then 13.5 g (3.5 equivalents) of 1,8-diazabicyclo[5.4.0]undeca-7-ene was added thereto. The resulting mixture was heated at about 100° C. for three hours with stirring, and then cooled to room temperature. Thereafter, the resulting solid substance was filtered off and sufficiently washed with ethanol. Thus, 4.55 g of 2-(p-nitrophenyl)-5-nitro-7-methoxybenzo[b]furan was obtained (yield: 70%).

4.6 g (1.0 equivalent) of the thus obtained 2-(p-nitrophenyl)-5-nitro-7-methoxybenzo[b]furan was added to 150 ml of a solvent mixture containing 1,4-dioxane and water in a ratio of 1:1 and 15.0 g (18.0 equivalents) of 100-mesh iron powder preliminarily activated with 0.5 ml of concentrated hydrochloric acid, and the resulting mixture was heated at about 110° C. for two hours under reflux with vigorous stirring. Immediately after the completion of the reaction was confirmed by way of TLC, the supernatant of the resulting reaction mixture was filtered in a hot state through a Celite filter. The residue was sufficiently washed with hot 1,4-dioxane and filtered away. After this filtration process was repeated three or four times, the filtrates were put together and concentrated by means of an evaporator. Thereafter, the resulting product was recrystallized from ethanol. Thus, 3.34 g of a pale orange product was obtained.

The product was analyzed by way of $^{13}$C-NMR. The results are as follows. Normal $^{13}$C-NMR (d-DMSO): 55.46 (OCH$_3$), 96.65 (CH), 95.89 (CH), 97.71 (CH), 113.85 (CH), 117.88 (C), 125.66 (CH), 131.42 (C), 136.14 (C), 144.45 (C), 145.27 (C), 149.26 (C), 156.39 (C).

DEPT135 $^{13}$C-NMR (d-DMSO): 55.46, 96.65, 96.89, 97.71, 113.85, 125.66.

The product was identified as 2-(p-aminophenyl)-5-amino-7-methoxybenzo[b]furan by the $^{13}$C-NMR analysis. The yield was 80%.

Figure 11:
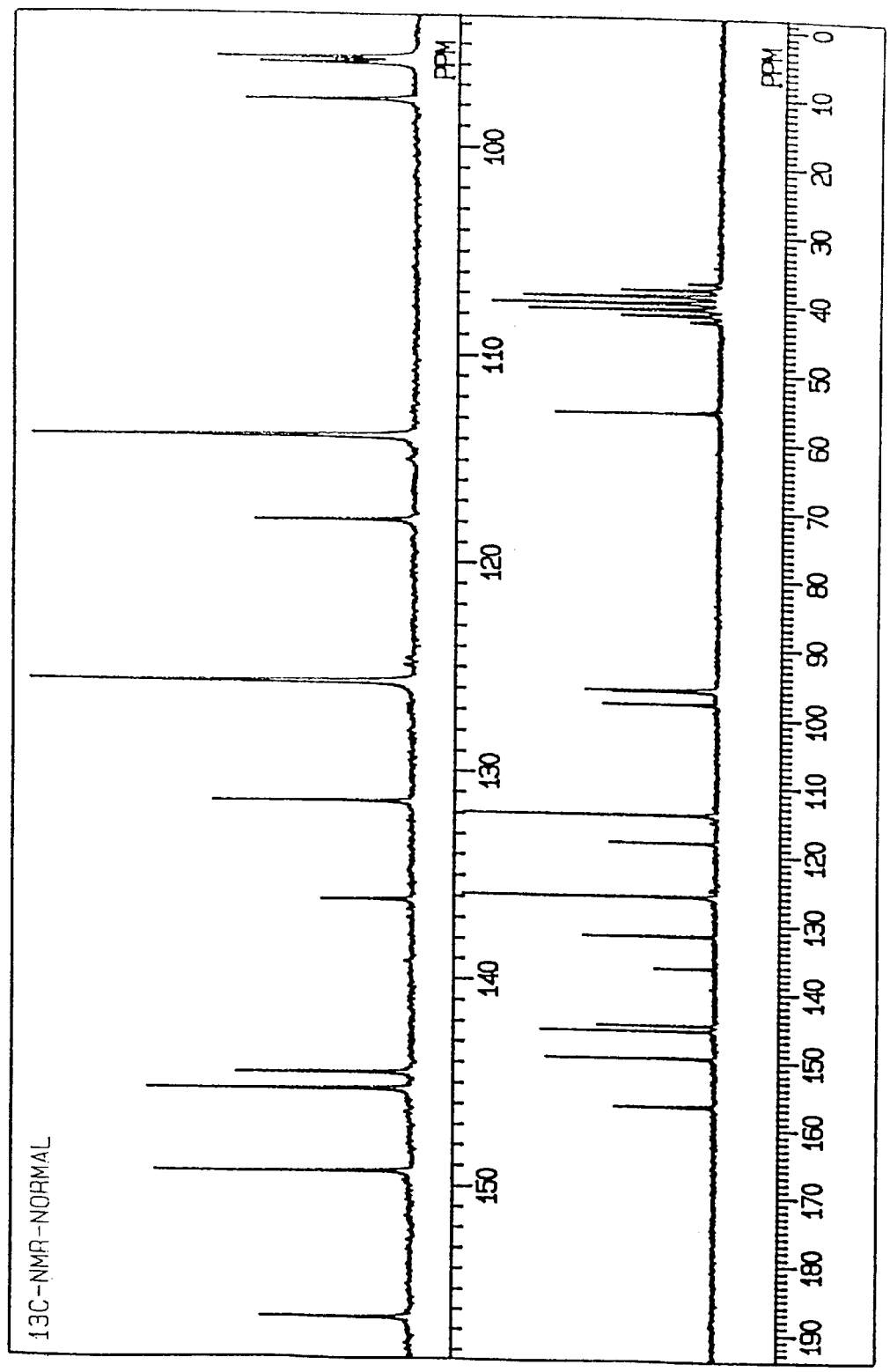
FIG. 11 is a chart of normal $^{13}$C-NMR spectrum of 2-(p-aminophenyl)-5-amino-7-methoxybenzo[b]furan of the present invention.
Figure 12:
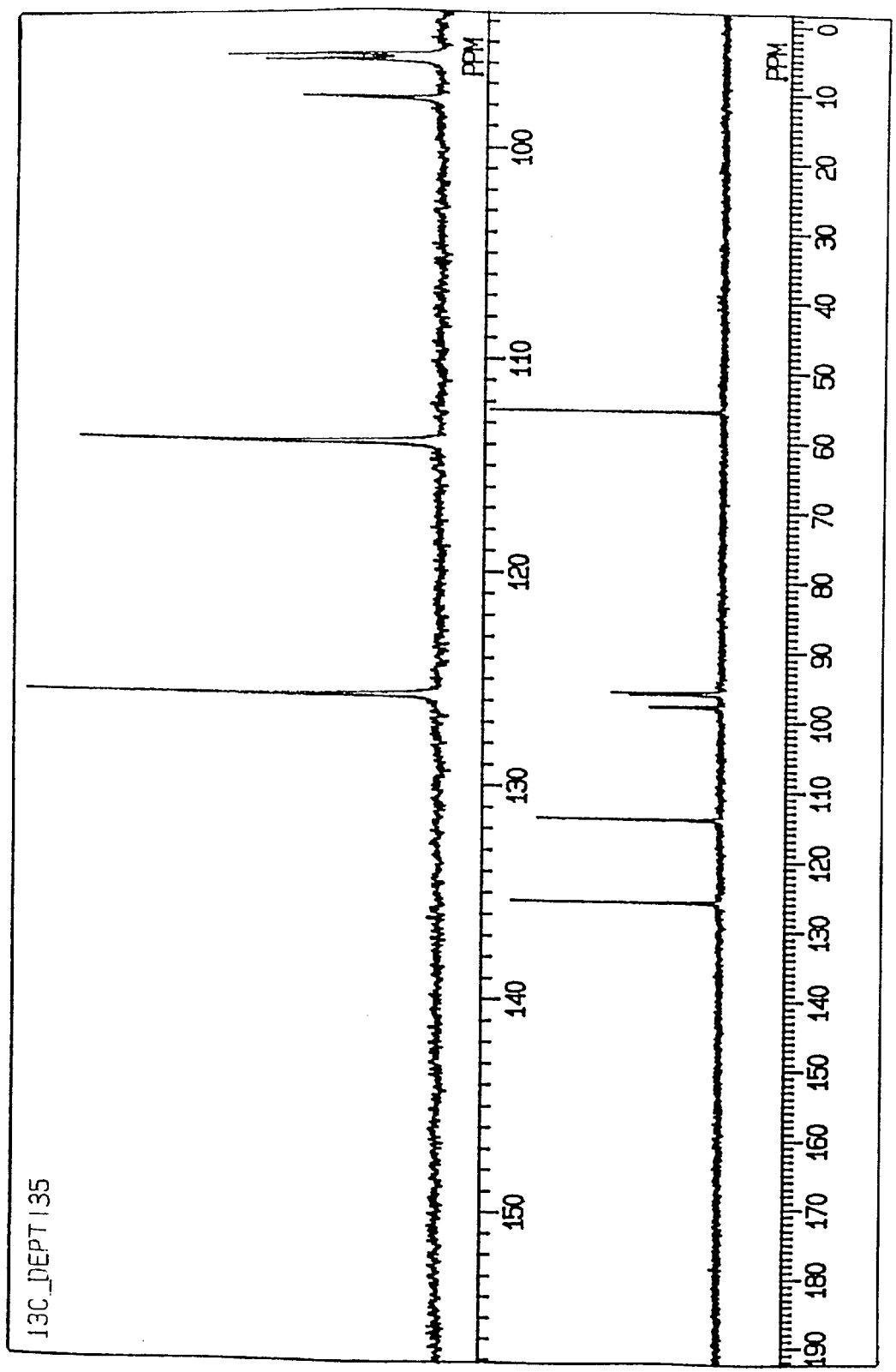
FIG. 12 is a chart of DEPO-135 $^{13}$C-NMR spectrum of 2-(p-aminophenyl)-5-amino-7-methoxybenzo[b]furan of the present invention.

It is noted that FIGS. 11 and 12 are charts of the normal $^{13}$C-NMR and the DEPT135 $^{13}$C-NMR, respectively, of 2-(p-aminophenyl)-5-amino-7-methoxybenzo[b]furan.

Synthesis Example 3

Synthesis of bis(tetrafluoroborate) salt of tetraazo form of 2-(p-aminophenyl)-5-aminobenzo[b]furan 470 mg (1.0 equivalent) of 2-(p-aminophenyl)-5-aminobenzo[b]furan was dissolved in 15 ml of 1N hydrochloric acid, and the resulting solution was cooled to 0° to 5° C. An aqueous solution containing 290 mg (2.11 equivalents) of sodium nitrite dissolved in 0.25 ml of water was gradually added to that resulting solution. The color of the solution immediately turned deep red. After the completion of the addition of the aqueous solution, the solution mixture was stirred at 0° to 5° C. for about 20 minutes for complete tetra-azotization of 2-(p-aminophenyl)-5-aminobenzo[b]furan. When an aqueous solution containing 480 mg (2.2 equivalents) of sodium tetrafluoroborate dissolved in 2.5 ml of water was added to the resulting tetraazo solution, a dark yellow solid substance of bis(tetrafluoroborate) salt of tetraazo form of 2-(p-aminophenyl)-5-aminobenzo [b]furan was precipitated. The solid substance was promptly filtered off and washed with a small amount of water. The solid substance containing a little moisture was put in a brown bottle and stored in a refrigerator for use in the subsequent step for a coupling reaction. The crude yield was 950 mg.

Synthesis Example 4

Synthesis of bis(tetrafluoroborate) salt of tetraazo form of 2-(p-aminophenyl)-5-amino-7-methoxybenzo[b]furan 510 mg (1.0 equivalent) of 2-(p-aminophenyl)5-amino-7-methoxybenzo[b]furan was dissolved in 15.5 ml of 1N hydrochloric acid, and the resulting solution was cooled to 0° to 5° C. An aqueous solution containing 291.2 mg (2.11 equivalents) of sodium nitrite dissolved in 0.25 ml of water was gradually added to that resulting solution. The color of the solution immediately turned deep red. After the completion of the addition of the aqueous solution, the solution mixture was stirred at 0° to 5° C. for about 20 minutes for complete tetra-azotization of 2-(p-aminophenyl)-5-amino-7-methoxybenzo[b]furan. When an aqueous solution containing 474.3 mg (2.2 equivalents) of sodium tetrafluoroborate dissolved in 2.5 ml of water was added to the resulting tetraazo solution, a deep red solid substance of bis(tetrafluoroborate) salt of tetraazo form of 2-(p-aminophenyl)-5-amino-7-methoxybenzo [b]furan was precipitated. The solid substance was promptly filtered off and washed with a small amount of water. The solid substance containing a little moisture was put in a brown bottle and stored in a refrigerator for use in the subsequent step for a coupling reaction. The crude yield was 1.2 g.

Synthesis Example 5
(Exemplary Compound No. 1)

400 mg (2.05 equivalents) of 3', 5'-bis(trifluoromethyl)-2-hydroxy-3-naphthanilide serving as a coupler component was dissolved in 30 ml of N,N-dimethylformamide, and the resulting solution was cooled to 0° to 5° C. A solution containing 240 mg of bis(tetrafluoroborate) salt of the tetraazo form of 2-(p-aminophenyl)-5-aminobenzo[b]furan (in a little moistened state; content>90%) dissolved in 5 ml of N,N-dimethylformamide was added to that resulting solution. A solution containing 0.2 ml (3.0 equivalents) of triethylamine dissolved in 5 ml of N,N-dimethylformamide was gradually added to the solution mixture. At this time, the color of the solution mixture turned dark blue. Thus, a bisazo compound No.1 was prepared. The compound was filtered off after it was allowed to stand in a refrigerator over night.

The bisazo compound thus prepared was washed with 150 ml of N,N-dimethylformamide three times, then with 150 ml of a solvent mixture containing acetone and water in a ratio of 1:1 once, and with 150 ml of acetone once. The purification of the bisazo compound was completed by thus repeating the washing and filtering process. Thereafter, the bisazo compound was dried at 80° C. for six hours. The yield was 380 mg.

Synthesis Examples 6 to 40 (Exemplary Compounds No. 2 to No. 36)

Exemplary Compounds No. 2 to No. 36 shown in Tables 1 to 6 were synthesized and purified in substantially the same manner as in Synthesis Example 5, except that couplers Cp1 ad Cp2 different from those used in Synthesis Example 5 were used.

TABLE 1

| Exemplary compound | R₁ | R₂ | Cp1 | Cp2 |
|---|---|---|---|---|
| 1 | H | H | 3-hydroxy-4-methyl-N-(3,5-bis(trifluoromethyl)phenyl)-2-naphthamide | Same as Cp1 |
| 2 | H | H | 2-(3,5-bis(trifluoromethyl)phenyl)-6-hydroxy-7-methyl-1H-benz[de]isoquinoline-1,3(2H)-dione | Same as Cp1 |
| 3 | H | H | benzimidazole-fused hydroxymethyl naphthalimide | Same as Cp1 |
| 4 | H | H | benzimidazole-fused hydroxymethyl naphthalimide | 3-hydroxy-4-methyl-N-(2-chlorophenyl)-2-naphthamide |
| 5 | H | H | 3-hydroxy-4-methyl-N-(2-chlorophenyl)-2-anthracenecarboxamide | Same as Cp1 |

TABLE 1-continued

[Structure: Cp1-N2 attached at position 5 of benzofuran system with (R1)n at position 7, (R2)m at position 9, and N2-Cp2 at position 11]

| Exemplary compound | R₁ | R₂ | Cp1 | Cp2 |
|---|---|---|---|---|
| 6 | H | H | [3-hydroxy-4-methyl-naphthalene-2-carboxamide with N-(2-chlorophenyl)] | Same as Cp1 |

TABLE 2

[Structure: Cp1-N2 attached at position 5 of benzofuran system with (R1)n at position 7, (R2)m at position 9, and N2-Cp2 at position 11]

| Exemplary compound | R₁ | R₂ | Cp1 | Cp1 |
|---|---|---|---|---|
| 7 | H | H | [3-hydroxy-4-methyl-naphthalene-2-carbohydrazide with =N-benzylidene bearing 3-CF₃] | Same as Cp1 |
| 8 | H | H | [3-hydroxy-4-methyl-naphthalene-2-carboxamide with N-(4-(N-(2-trifluoromethylphenyl)carbamoyl)phenyl)] | Same as Cp1 |
| 9 | H | H | [3-hydroxy-4-methyl-2-(benzoxazol-2-yl)naphthalene] | Same as Cp1 |

TABLE 2-continued

| Exemplary compound | R₁ | R₂ | Cp1 | Cp1 |
|---|---|---|---|---|
| 10 | 7-OCH₃ | H | (structure) | (structure) |
| 11 | 7-OCH₃ | H | (structure) | Same as Cp1 |
| 12 | 7-OCH₃ | H | (structure) | Same as Cp1 |

TABLE 3

| Exemplary compound | R₁ | R₂ | Cp1 | Cp1 |
|---|---|---|---|---|
| 13 | 7-OCH₃ | H | (structure) | Same as Cp1 |

TABLE 3-continued
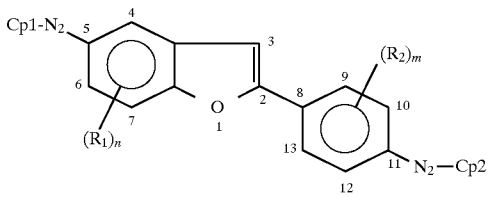
| Exemplary compound | R₁ | R₂ | Cp1 | Cp1 |
|---|---|---|---|---|
| 14 | 7-OCH₃ | H | 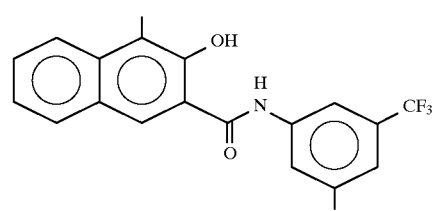 | Same as Cp1 |
| 15 | 7-OCH₃ | 9-Cl | 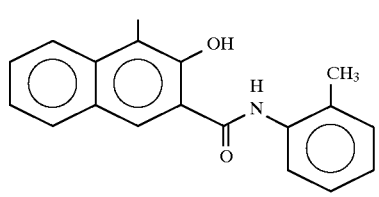 | Same as Cp1 |
| 16 | 7-OCH₃ | 9-Cl | 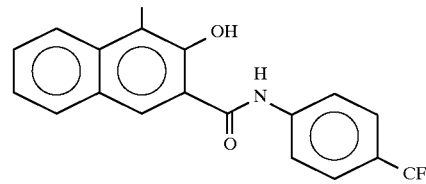 | Same as Cp1 |
| 17 | 7-OCH₃ | 9-Cl | 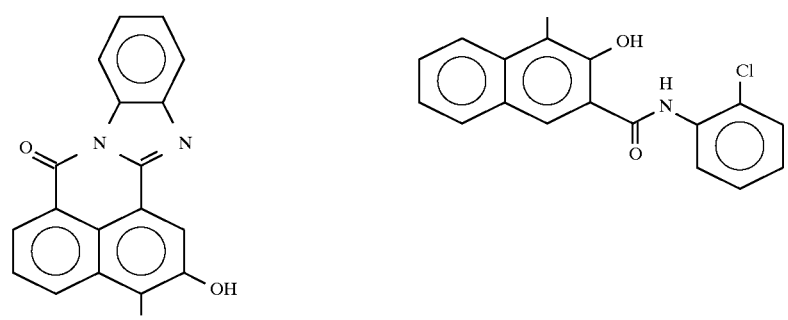 | 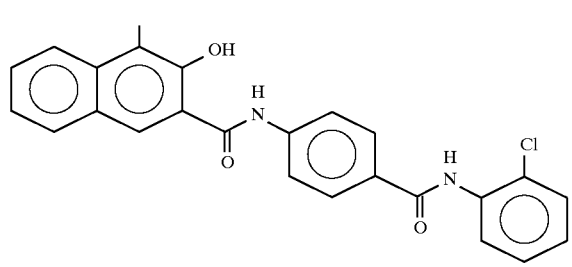 |
| 18 | 7-OCH₃ | 9-Cl |  | Same as Cp1 |

TABLE 4

| Exemplary compound | R₁ | R₂ | Cp1 | Cp1 |
|---|---|---|---|---|
| 19 | H | 9-Cl | [naphthol with benzimidazole substituent] | Same as Cp1 |
| 20 | H | 9-Cl | [3-hydroxy-4-methyl-2-naphthoyl o-toluidide] | Same as Cp1 |
| 21 | H | 9-Cl | [naphthol with benzothiazole substituent] | Same as Cp1 |
| 22 | H | 9-Cl | [bis-naphthalimide type structure with benzimidazole] | [3-hydroxy-4-methyl-N-(2-chlorophenyl)-2-naphthamide] |
| 23 | H | 9-Cl | [3-hydroxy-4-methyl-N-(3,5-bis(trifluoromethyl)phenyl)-2-naphthamide] | Same as Cp1 |
| 24 | H | 9-Cl | [3-hydroxy-4-methyl-2-naphthamide-phenyl-N-(2-chlorophenyl)carboxamide] | Same as Cp1 |

TABLE 5

| Exemplary compound | R₁ | R₂ | Cp1 | Cp1 |
|---|---|---|---|---|
| 25 | H | 9-Cl | 3-hydroxy-4-methyl-N-(2-chlorophenyl)-2-naphthamide | Same as Cp1 |
| 26 | 7-CF₃ | H | 3-hydroxy-4-methyl-N-(2-chlorophenyl)-2-naphthamide | Same as Cp1 |
| 27 | 7-CF₃ | H | 3-hydroxy-4-methyl-N-(3,5-bis(trifluoromethyl)phenyl)-2-naphthamide | Same as Cp1 |
| 28 | 7-OC₂H₅ | H | 3-hydroxy-4-methyl-N-(3-trifluoromethylphenyl)-2-naphthamide | Same as Cp1 |
| 29 | 7-OC₂H₅ | H | 3-hydroxy-4-methyl-N-(4-((3,5-bis(trifluoromethyl)phenyl)azo)phenyl)-2-naphthamide | Same as Cp1 |
| 30 | 7-Cl | H | 3-(benzimidazol-2-yl)-4-methyl-2-naphthol | Same as Cp1 |

TABLE 6

| Exemplary compound | R₁ | R₂ | Cp1 | Cp1 |
|---|---|---|---|---|
| 31 | 7-Cl | H | 3-hydroxy-4-methyl-N-[4-(2-chlorobenzamido)phenyl]-2-naphthamide | Same as Cp1 |
| 32 | 7-CH₃ | H | 3-hydroxy-4-methyl-N-[4-(trifluoromethyl)phenyl]-2-naphthamide | Same as Cp1 |
| 33 | 7-CH₃ | H | 3-hydroxy-4-methyl-N-{4-[(4-chlorophenyl)azo]phenyl}-2-naphthamide | Same as Cp1 |
| 34 | 7-CH₃ | 9-Cl | 3-hydroxy-4-methyl-N-(4-{[2-(trifluoromethyl)phenyl]carbamoyl}phenyl)-2-naphthamide | Same as Cp1 |
| 35 | 7-CH₃ | 9-Cl | 3-hydroxy-4-methyl-N-{4-[(3-trifluoromethylphenyl)azo]phenyl}-2-naphthamide | Same as Cp1 |

TABLE 6-continued

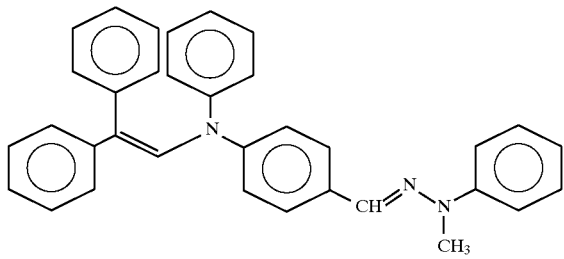

| Exemplary compound | $R_1$ | $R_2$ | Cp1 | Cp1 |
|---|---|---|---|---|
| 36 | 7-$CH_3$ | 9-Cl | (structure shown) | Same as Cp1 |

EXAMPLE 1

A 80 μm-thick polyester film having an aluminum layer deposited thereon was used as a support base. The bisazo compound No. 3 of the present invention was added to a 1% DME solution containing a polyvinyl butyral resin (ESRECK B available from Nisshin Chemical Industry Co.) in the same weight as the resin, and dispersed therein for about five hours along with zirconium beads having a diameter of 1.5 mm in a paint conditioner (manufactured by Red Level Inc.) for preparation of a coating liquid. The coating liquid was applied on the support base by means of a doctor blade, and dried. The thickness of the dried coating was 0.2 μm.

A pigment layer (charge carrier generating layer) thus formed was coated with a solution containing 1 g of a hydrazone compound of the following structural formula and 1.2 g of a polyarylate resin (U-100 available from Unitica) dissolved in methylene chloride by means of a squeeging doctor.

Thus, a resin-hydrazone compound solid solution layer (charge carrier transferring layer) was formed which had a thickness of 25 μm in a dried state.

The electrophotographic characteristics of a laminate electrophotographic photoconductor thus produced were evaluated by means of an electrostatic recording paper test apparatus (EPA-8200 manufactured by Kawaguchi Electric Co.). For the measurement, a 10 μA constant current system and a statistic system No. 3 were employed. The initial potential V0 (–volt) of the electrophotographic photoconductor and an exposure light amount E1/2 (lux.sec) required for reducing the potential from –500V to –250V by white illumination (5 lux) were measured. After 500 cycles of the aforesaid measurement process were conducted, the electrophotographic characteristics were determined in the same manner.

The results are shown in Table 8.

Examples 2 to 10

Nine different electrophotographic photoconductors were produced in substantially the same manner as in Example 1, except that other exemplary compounds of the present invention were used as charge carrier generating substances. The aforesaid characteristic test was performed on these electrophotographic photoconductors.

The results are shown in Table 8.

Comparative Examples 1 to 3

Three different electrophotographic photoconductors were produced in substantially the same manner as in Example 1, except that compounds of the following structural formulae (a) to (c) (see Table 7) disclosed in Japanese Unexamined Patent Publication No. 5-173344 (1993) were used as charge carrier generating substances.

The aforesaid characteristic test was performed on these electrophotographic photoconductors.

The results are shown in Table 7.

TABLE 7

| | $K^1$, $K^2$ | $R_1$ |
|---|---|---|
| Com. Ex. 1 (structural formula (a)) | (structure shown) | H |

TABLE 7-continued

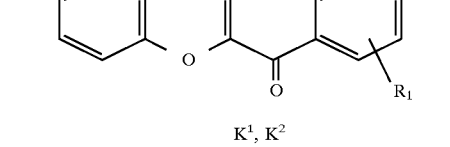

| | K¹, K² | R₁ |
|---|---|---|
| Com. Ex. 2 (structural formula (b)) | 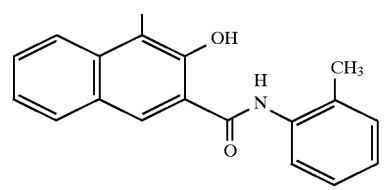 | H |
| Com. Ex. 3 (structural formula (c)) | 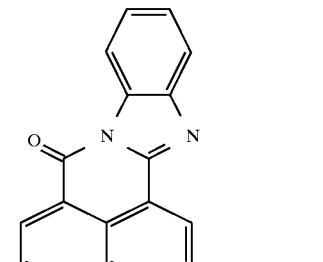 | H |

TABLE 8

| | | Initial | | After 500 cycles | |
|---|---|---|---|---|---|
| Example | Exemplary Compound | VO (-V) | E½ (lux · sec) | VO (-V) | E½ (lux · sec) |
| Ex.1 | 1 | 670 | 2.2 | 660 | 2.2 |
| Ex.2 | 6 | 630 | 3.1 | 610 | 3.3 |
| Ex.3 | 11 | 650 | 3.6 | 620 | 3.8 |
| Ex.4 | 14 | 700 | 2.3 | 680 | 2.4 |
| Ex.5 | 23 | 580 | 3.9 | 570 | 4.1 |
| Ex.6 | 25 | 650 | 2.7 | 620 | 2.9 |
| Ex.7 | 28 | 690 | 2.0 | 660 | 2.2 |
| Ex.8 | 29 | 640 | 2.8 | 620 | 3.0 |
| Ex.9 | 32 | 610 | 3.1 | 580 | 3.3 |
| Ex.10 | 35 | 720 | 2.3 | 700 | 2.4 |
| Com.Ex.1 | a | 580 | 4.2 | 550 | 4.4 |
| Com.Ex.2 | b | 600 | 4.8 | 570 | 5.0 |
| Com.Ex.3 | c | 530 | 5.1 | 500 | 5.5 |

Table 8 indicates that the bisazo compounds of the present invention offered an excellent photosensitivity and repetition characteristics.

The bisazo compound of the general formula (I) useful as a charge carrier generating substance for an electrophotographic photoconductor according to the present invention is capable of efficiently generating charge carriers without being influenced by external factors such as temperature and humidity even after repetitive use. Therefore, the electrophotographic photoconductor of the present invention which uses such a bisazo compound is excellent in the stability and the charging characteristics, and is free from the reduction in the photosensitivity due to repetitive use thereof.

The bisazo compound of the present invention can be used alone or in combination with a charge carrier transferring substance in a photosensitive layer, providing a charge carrier generating substance for an electrophotographic photoconductor with a great applicability.

Further, the processes for producing 2-(nitrophenyl) nitrobenzo[b]furan and 2-(aminophenyl) aminobenzo[b] furan derivatives and the process for producing the bisazo compound of the present invention from these derivatives in accordance with the present invention provide the respective target compounds with high yields and, in addition, posttreatment processes required after the reactions are simple. Thus, the simple production processes with high yields are provided by the present invention.

Moreover, the electrophotographic photoconductor of the present invention is excellent in the charging characteristics, the photosensitivity and the durability, and is free from the reduction in the photosensitivity which would otherwise occur through repetitive use thereof.

What is claimed is:

1. An electrophotographic photoconductor comprising as a charge carrier generating substance a bisazo compound of the general formula (I):

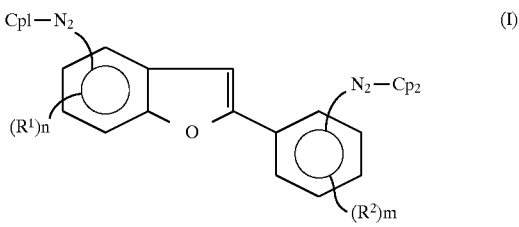

(I)

wherein R¹ and R² are the same or different, each representing a hydrogen atom, a halogen atom, a lower alkyl group optionally substituted with a fluorine atom, an aralkyl group optionally having a substituent, a lower alkoxy group, or a di-(lower alkyl)amino group; n is an integer from 1 to 3; m is an integer from 1 to 4; and Cp1 and Cp2 are the same or different, each representing an aromatic condensed heterocyclic or aromatic condensed hydrocarbon residue having at least one phenolic hydroxyl group and optionally having a substituted carbamoyl group or a heterocyclic group.

2. An electrophotographic photoconductor as set forth in claim 1, wherein the general formula (I) is represented by the general formula (I)':

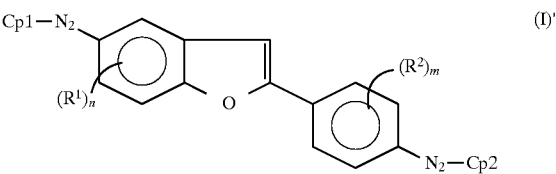

(I)' wherein R¹, R², n, m, Cp1 and Cp2 each have the same definition as in the general formula (I).

3. An electrophotographic photoconductor as set forth in claim 1, wherein R¹ and R² each represent a hydrogen atom, a chlorine atom, a methyl group, a methoxy group, an ethoxy group or a trifluoromethyl group.

4. An electrophotographic photoconductor as set forth in claim 1, wherein Cp1 and Cp2 each represent by the general formulae (VII-1) to (VII-6):

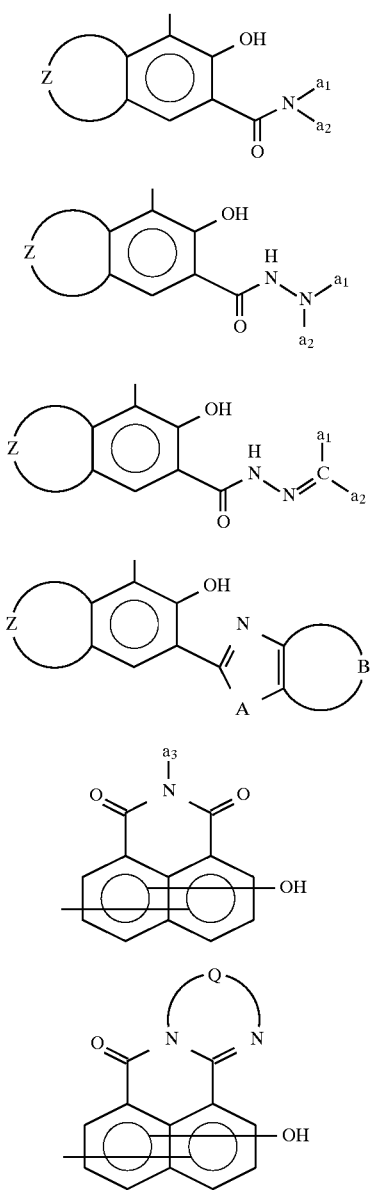

(VII-1)
(VII-2)
(VII-3)
(VII-4)
(VII-5)
(VII-6)

wherein Z is an atomic group which is required for formation of an aromatic polycyclic group such as a naphthalene ring or anthracene ring resulting from condensation with a benzene ring, or an aromatic heterocyclic group such as a carbazole ring, dibenzocarbazole ring, dibenzofuran ring or fluorene ring resulting from condensation with a benzene ring; Q is a divalent linear hydrocarbon group or aromatic hydrocarbon group required for formation of a five-membered ring or a six-membered ring, or a divalent aromatic heterocyclic group having a nitrogen atom in its ring; A is an oxygen atom, a sulfur atom, or an N-a4 group (wherein a4 is a hydrogen atom, or a lower alkyl group, an aromatic hydrocarbon group or a lower aralkyl group, optionally having a substituent); B is a divalent residue required for formation of an aromatic hydrocarbon group by condensation with a carbon double bond; a1 and a2 are independent, each representing a hydrogen atom (excluding a case where a1 and a2 are both hydrogen atoms), or a lower alkyl group, an aromatic hydrocarbon group, an aralkyl group or an aromatic heterocyclic group, optionally having a substituent; a3 is a lower alkyl group, an aromatic hydrocarbon group, an aralkyl group or an aromatic heterocyclic group, optionally having a substituent.

5. An electrophotographic photoconductor as set forth in claim 4, wherein the group Z is a residue derived form benzene, naphthalene or carbazole, the group Q is phenylene, the groups a1 and a2 are a hydrogen atom, chlorophenyl, trifluorophenyl, tolyl or ethylphenyl, the group a3 is di- or tri-fluorophenyl, the group A is an oxygen atom or a sulfur atom, and the group B is phenylene.

6. An electrophotographic photoconductor as set forth in claim 1, wherein the bisazo compound is selected from the following compounds

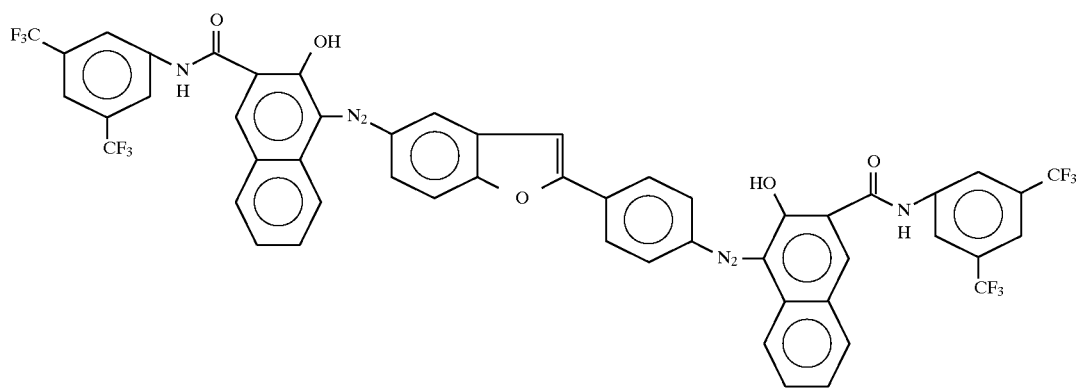

-continued
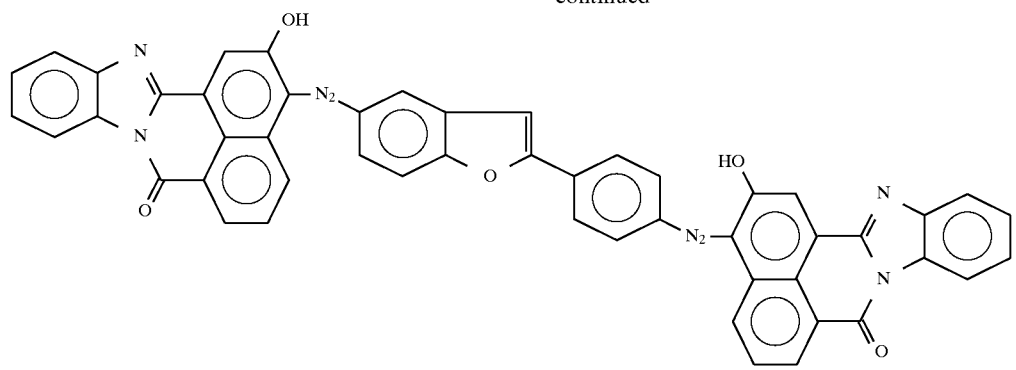
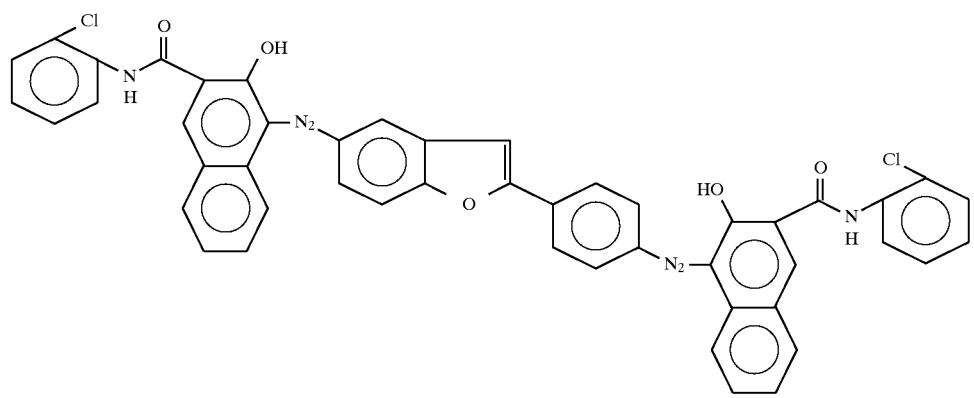
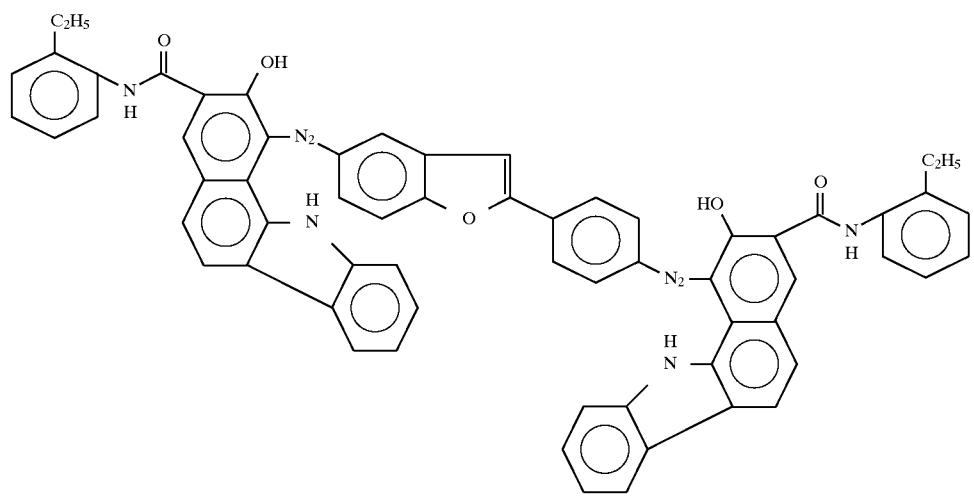
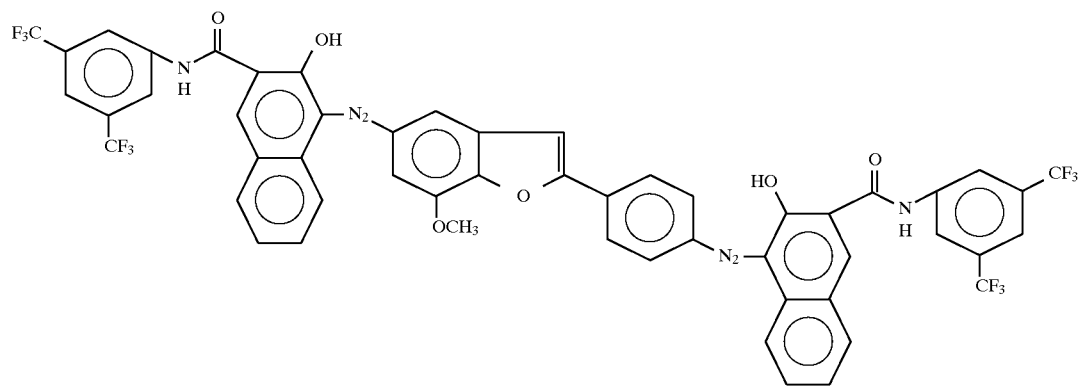

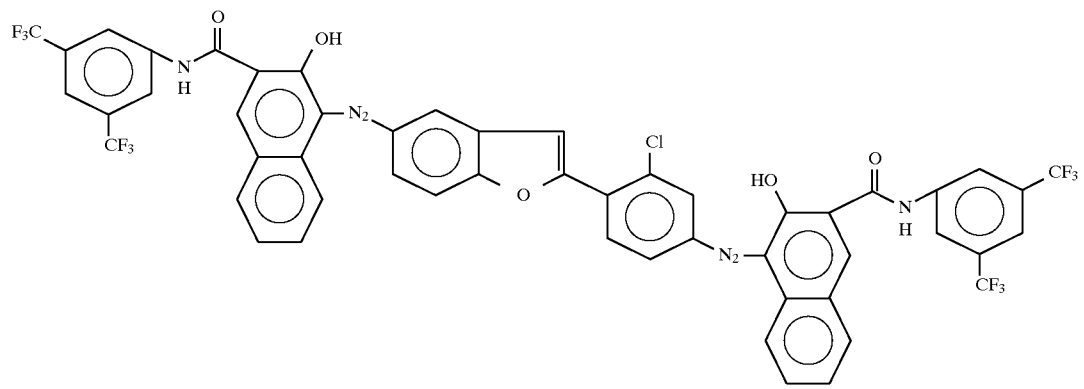
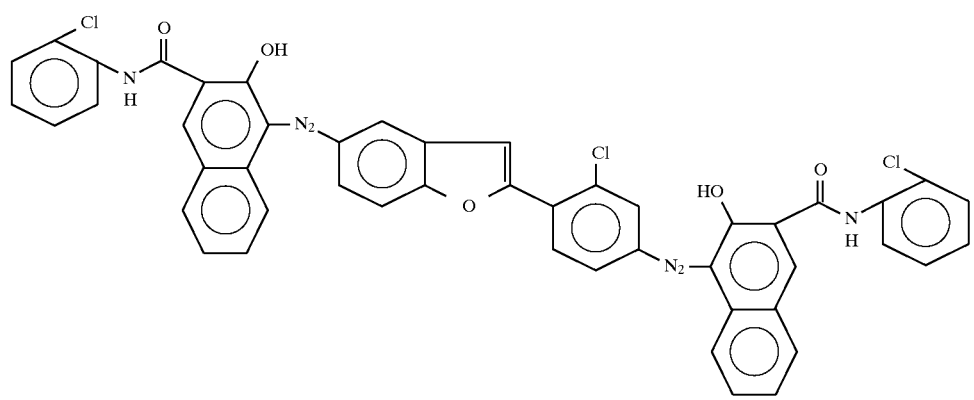
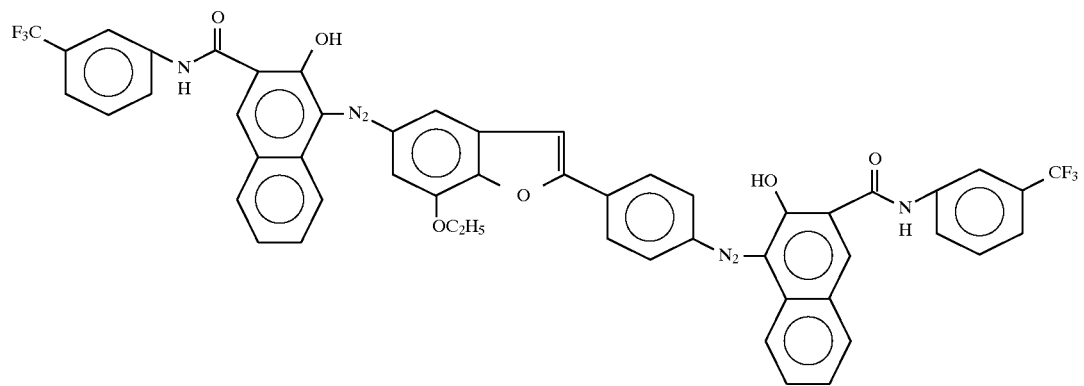
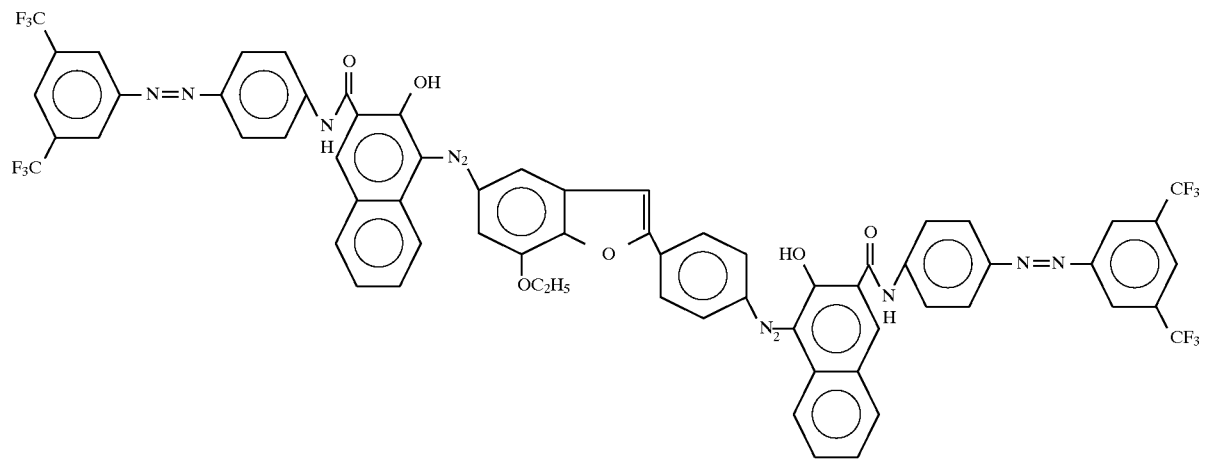

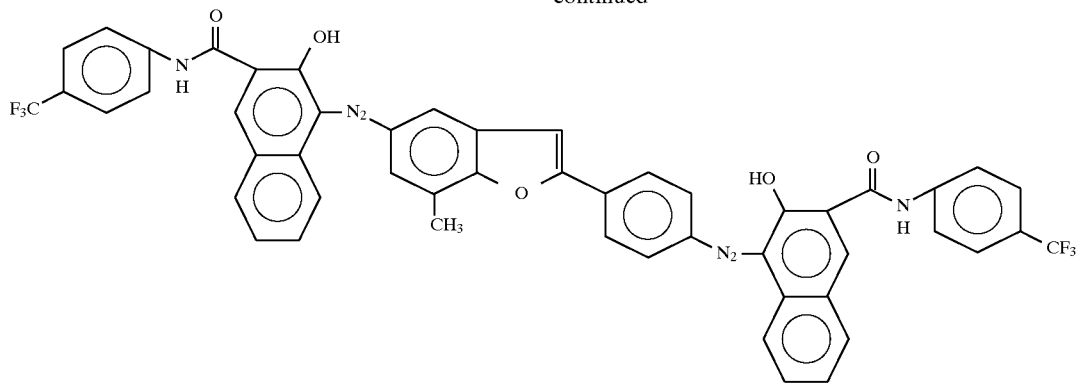

and

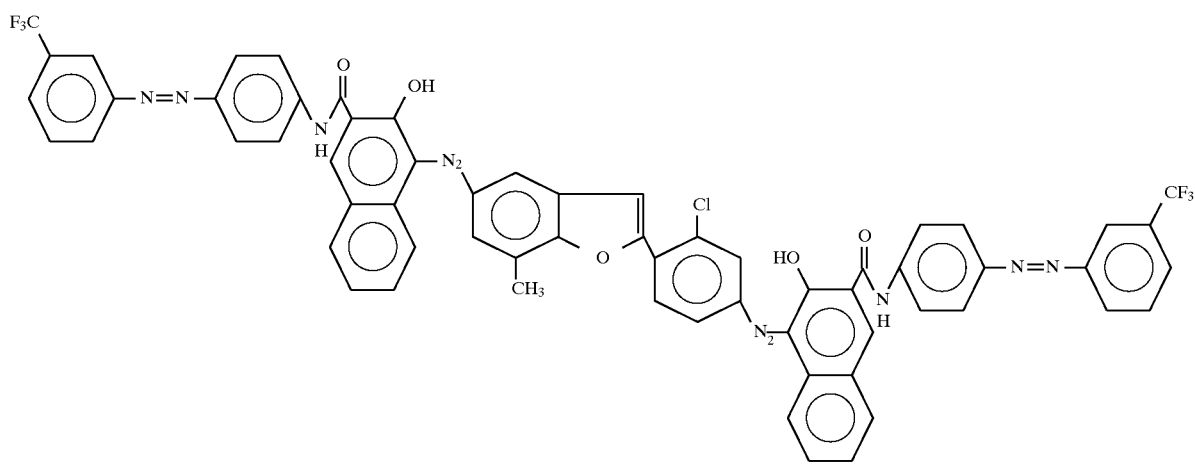

7. An electrophotographic photoconductor as set forth in claim 1, which is a single-layer type electrophotographic photoconductor comprising:
   a conductive support base; and
   a layer formed on the conductive support base and containing the charge carrier generating substance of formula (I) and a charge carrier transferring substance.

8. An electrophotographic photoconductor as set forth in claim 1, which is a function-separated type electrophotographic photoconductor comprising:
   a conductive support base;
   a charge carrier generating layer containing the charge carrier generating substance of the formula (I); and
   a charge carrier transferring layer containing a charge carrier transferring substance;
   the charge carrier generating layer and the charge carrier transferring layer being stacked on the conductive support base.

9. An electrophotographic photoconductor as set forth in claim 1, wherein $R^1$ is a hydrogen atom, a chlorine atom, a methyl group, a methoxy group, an ethoxy group or a trifluoromethyl group, $R^2$ is a hydrogen atom or a chlorine atom, and $Cp^1$ and $Cp^2$ are the same or different, each representing

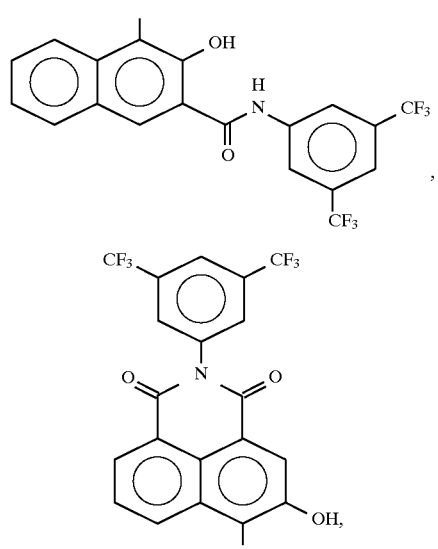

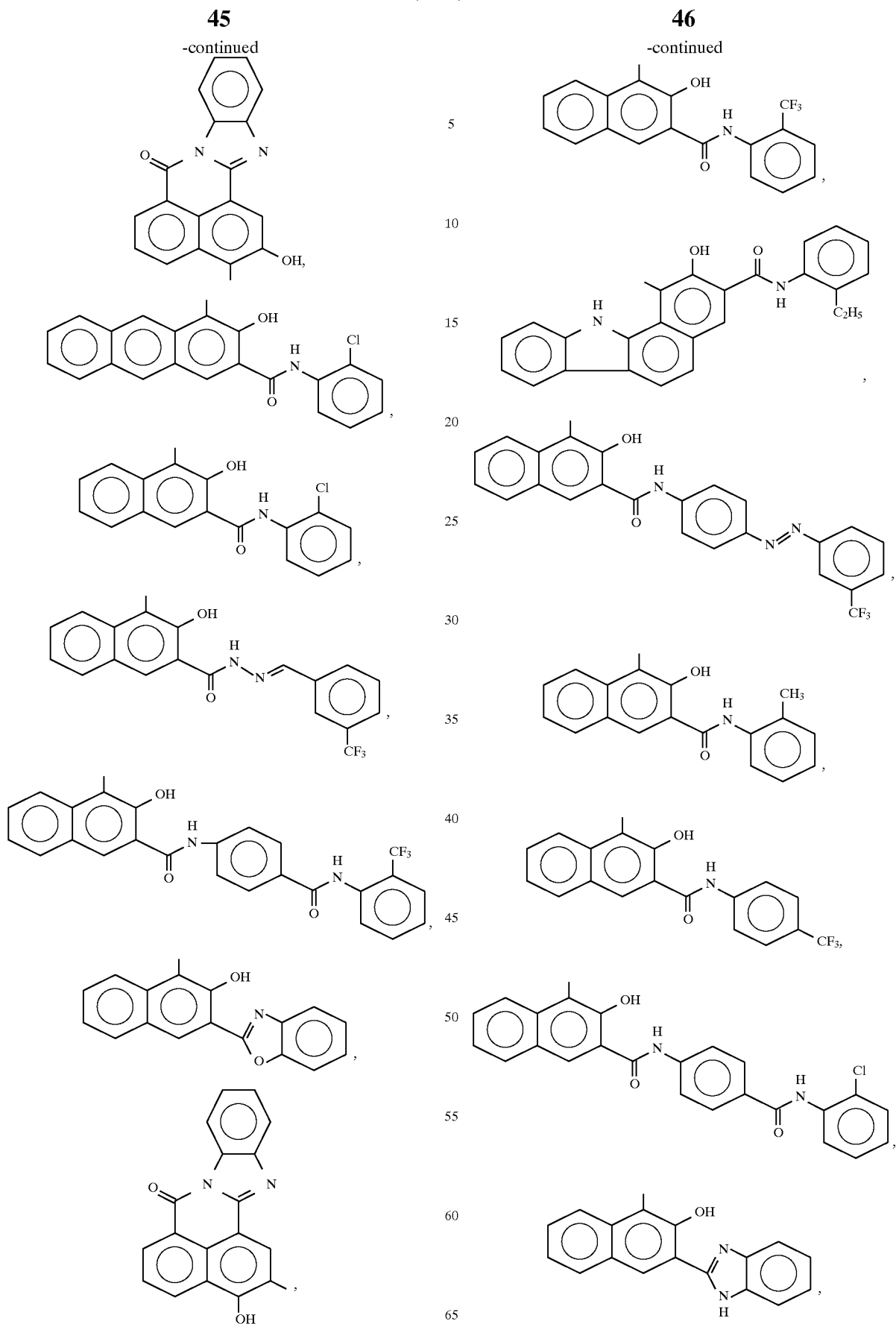

47
-continued
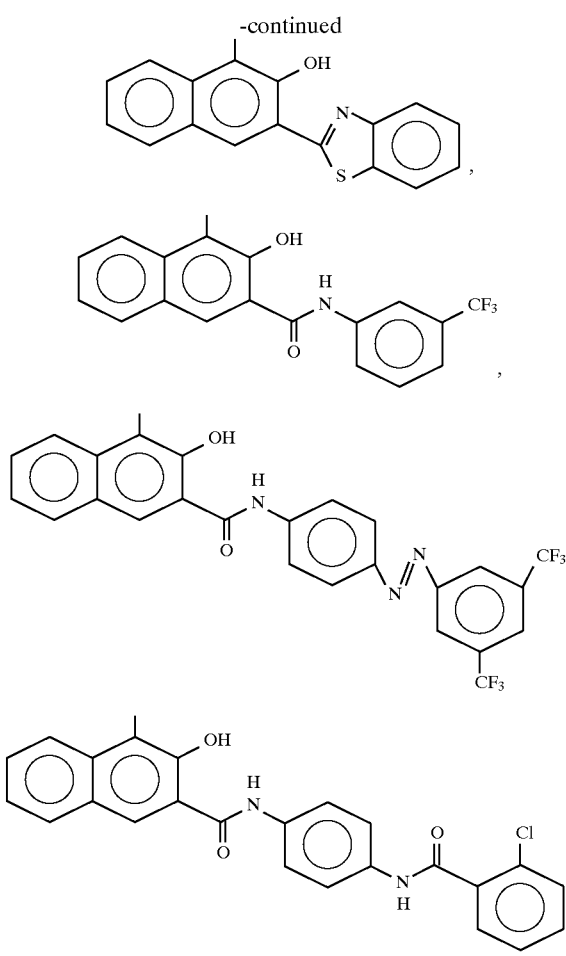
48
-continued
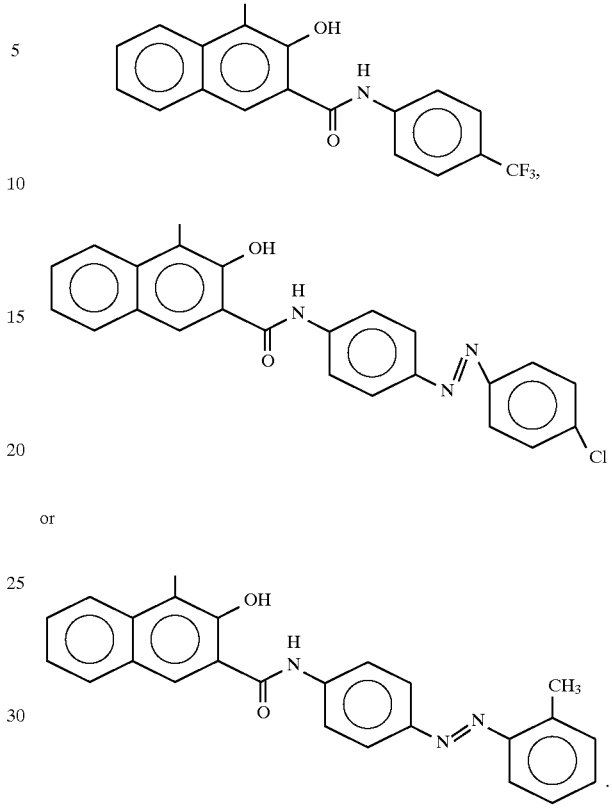
* * * * *